(12) United States Patent
Lal et al.

(10) Patent No.: US 7,166,572 B1
(45) Date of Patent: Jan. 23, 2007

(54) CYCLOHEXAPEPTIDE COMPOUNDS, PROCESSES FOR THEIR PRODUCTION AND THEIR USE AS A PHARMACEUTICAL

(75) Inventors: Bansi Lal, Mumbai (IN); Vitthal G. Gund, Sherbrooke (CA); Ashok K. Gangopadhyay, Mumbai (IN)

(73) Assignee: Aventis Pharma Deutschland GmbH, Frankfurt (DE)

( * ) Notice: Subject to any disclaimer, the term of this patent is extended or adjusted under 35 U.S.C. 154(b) by 501 days.

(21) Appl. No.: 10/031,764

(22) PCT Filed: Jul. 15, 2000

(86) PCT No.: PCT/EP00/06769

§ 371 (c)(1),
(2), (4) Date: Sep. 30, 2002

(87) PCT Pub. No.: WO01/07468

PCT Pub. Date: Feb. 1, 2001

(30) Foreign Application Priority Data

Jul. 27, 1999 (EP) .................................. 99114649

(51) Int. Cl.
*A61K 38/00* (2006.01)
(52) U.S. Cl. .......................................................... 514/9
(58) Field of Classification Search .................. 514/9
See application file for complete search history.

(56) References Cited

U.S. PATENT DOCUMENTS

| 5,378,804 A * | 1/1995 | Balkovec et al. ............ 530/317 |
| 5,541,160 A * | 7/1996 | Balkovec et al. ............. 514/11 |
| 5,914,313 A | 6/1999 | Bouffard |

FOREIGN PATENT DOCUMENTS

| WO | 9421677 | 9/1994 |
| WO | 9527074 | 10/1995 |
| WO | 9611210 | 4/1996 |
| WO | 9622784 | 8/1996 |

OTHER PUBLICATIONS

"Synthesis . . . Pneumonia", Journal of Medicinal Chemistry, US, American Chemical Society, Washington, vol. 35, No. 1, Jan. 10, 1992, pp. 194-198.
"Mulundocandin . . . Antibiotic", Journal of Antibiotics, vol. XL, No. 8, Mar. 1987, pp. 275-280.

* cited by examiner

*Primary Examiner*—Bruce R. Campell
*Assistant Examiner*—Maury Audet
(74) *Attorney, Agent, or Firm*—Balaram Gupta

(57) ABSTRACT

A cyclohexapeptide compound of general formula (I), wherein $R^1$ is $C_1$–$C_{20}$ alkyl; $C_9$–$C_{20}$ alkenyl; $C_9$–$C_{20}$ alkoxyphenyl; an aryl group selected from: phenyl, biphenyl, terphenyl and naphthyl; $C_1$–$C_{12}$ alkylphenyl, $C_2$–$C_{12}$ alkenylphenyl, $C_1$–$C_{12}$ alkoxyphenyl; linoleoyl; palmitoyl; 12-methylmyristoyl; 10,12-dimethylmyristoyl; or —$COC_6H_4(p)OC_8H_{17}$, $R_1$ and $R_3$ are independently —OH; —CN; —$CH_2NH_2$; —$N_3$; aryl; substituted aryl; heterocyclyl and substituted heterocyclic with 1–3 of the same or different heteroatoms; aminoalkylamino; mono or di-substituted linear or cyclic aminoalkylamino; —OR, wherein, R is $C_1$–$C_{12}$ alkyl; substituted alkyl of the type —$(CH_2)_n$—X, where n is 1–5 and X is Cl, Br, I, COOY, CN, $NH_2$ or a heterocyclic and where Y is $C_1$–$C_6$ linear or branched alkyl; $C_2$–$C_{12}$-alkenyl; aryl; fused aryl; substituted aryl; a heterocyclic containing 1–3 heteroatoms; mono or di-substituted aminoalkyl; or a hydroxy protecting group; and $R_3$ may additionally be imidazolyl; $R_2$ and $R_4$ are independently —H or —OH; $R_5$ is —H or —$CH_3$, $R_6$ is —H, —$CH_3$ or —$CH_2CONH_2$. $R_7$ is —H, —$CH_3$ or —OH. $R_8$ and $R_9$ are independently —H or —$CH_2$-Sec.amine in which the sec.amine is attached to —$CH_2$ through its N linkage; and its pharmaceutically acceptable salts. The compounds are useful as antifungal agents.

9 Claims, No Drawings

CYCLOHEXAPEPTIDE COMPOUNDS, PROCESSES FOR THEIR PRODUCTION AND THEIR USE AS A PHARMACEUTICAL

This application is a 371 of PCT/EP00/06769 filed Jul. 15, 2000.

Novel cyclohexapeptide compounds, processes for their production and their use as a pharmaceutical.

The present invention relates to cyclohexapeptide compounds belonging to the echinocandin class having a substituent group at the ornithine-5, homotyrosine-4 and ortho position of the phenolic hydroxy of the homotyrosine unit, and pharmaceutically acceptable salts thereof. The present invention further relates to processes for the preparation of the novel cyclohexapeptide compounds, to the use of the compounds and their pharmaceutically acceptable salts as pharmaceuticals, in particular to their use in the treatment of fungal infections, and to pharmaceutical compositions comprising the novel compounds or a pharmaceutically acceptable salt thereof.

The search for new and effective antifungal agents has been intensified by the increase in immunological diseases and aggressive immunosuppressive chemotherapy. Present therapeutic options for the treatment of fungal infections are limited to compounds in two classes, the polyenes and the azoles. Due to an increase in the number of isolates, which are resistant to conventional antifungal agents, there presently exists a need for new antifungal and anti-pneumocystis agents. Because there are limited numbers of antifungal agents available for the treatment of life-threatening fungal infections and because resistance may further limit the utility of the newer azoles, there is an urgent need for new antifungal agents with a different mode of action.

Accordingly, the present invention provides novel antifungal cyclohexapeptide compounds represented by general formula I as shown below:

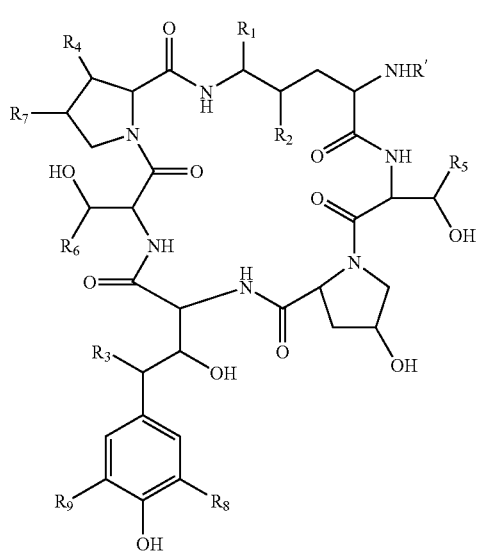

I wherein $R^1$ is $C_9$–$C_{20}$ alkyl; $C_9$–$C_{20}$ alkenyl; $C_9$–$C_{20}$ alkoxyphenyl; an aryl group selected from: phenyl, biphenyl, terphenyl and naphthyl; $C_1$–$C_{12}$ alkylphenyl, $C_2$–$C_{12}$ alkenylphenyl, $C_1$–$C_{12}$ alkoxyphenyl; linoleoyl; palmitoyl; 12-methylmyristoyl; 10,12-dimethylmyristoyl; or —$COC_6H_4(p)OC_8H_{17}$;

$R_1$ and $R_3$ are independently —H; —OH; —CN; —$CH_2NH_2$; —$N_3$; aryl; substituted aryl; heterocyclyl and substituted heterocyclyl with 1–3 of the same or different heteroatoms; aminoalkylamino; mono or di-substituted linear or cyclic aminoalkylamino; —OR, wherein, R is $C_1$–$C_{12}$ alkyl; substituted alkyl of the type —$(CH_2)_n$—X, where n is 1–5 and X is Cl, Br, I, COOY, CN, $NH_2$ or a heterocyclic and where Y=$C_1$–$C_6$ linear or branched alkyl; $C_2$–$C_{12}$-alkenyl; aryl; fused aryl; substituted aryl; a heterocyclic containing 1–3 heteroatoms; mono or di-substituted aminoalkyl; or a hydroxy protecting group; or $R_3$ is imidazolyl;

$R_2$ and $R_4$ are independently —H or —OH;

$R_5$ is —H or —$CH_3$.

$R_6$ is —H, —$CH_3$ or —$CH_2CONH_2$, $R_7$ is —H, —$CH_3$ or —OH;

$R_8$ and $R_9$ are independently —H or —$CH_2$-Secondary amine, the secondary amine being attached to —$CH_2$ through its N-linkage; and its pharmaceutically acceptable salts.

To the nitrogen atom of the secondary amine are attached the same or different groups selected from: $C_1$–$C_{12}$ alkyl, $C_2$–$C_{12}$ alkenyl, aryl, substituted aryl, alkylaryl and substituted alkylaryl, or the nitrogen atom of the secondary amine is part of a heterocyclic group, optionally substituted by one or more of: $C_1$–$C_6$ alkyl, $C_2$–$C_6$ alkenyl, aryl, amino, nitro and halogen, or a fused heterocyclic group, whereby the heterocyclic group in each case contains 1–3 of the same or different heteroatoms.

Examples of suitable secondary amines are piperidine, pyrrolidine, 4-methyl-piperidine, morpholine, dimethylamine, diisopropylamie, 4-piperidino-piperidine, piperazine, 1-methylpiperazine, 1-(2-fluorophenyl)piperazine, 1-(2-chlorophenyl)piperazine, 1-(2-pyrimidyl)piperazine, 1-(4-fluorophenyl)piperazine, N-(α,α,α-trifluoro-m-tolyl) piperazine, 1-phenylpiperazine, 1-benzylpiperazine, 1-(2-pyridyl)piperazine, 1-(4-pyridyl)piperazine, 1-(4-methylphenyl) piperazine, 1-(2,6-dimethylphenyl)piperazine, 1-(1-phenylethyl)piperazine, dibenzylamine, N-(tert-butyl)benzylamine, and N-(isopropyl)benzylamine.

In a preferred first embodiment, $R_1$ is —OH or —OR and $R_3$ is —OH, —OR or imidazolyl, wherein R in each case is $C_1$–$C_{12}$ alkyl, substituted alkyl of the type —$(CH_2)_n$—X, where n is 1–5, X is Cl, Br, I, COOY, CN, $NH_2$ or a heterocyclic and Y is a $C_1$–$C_6$ linear or branched alkyl; $C_2$–$CO_2$-alkenyl; aryl; fused aryl; substituted aryl; a heterocyclic containing 1–3 heteroatoms; mono or di-substituted aminoalkyl; or a hydroxy protecting group.

Ideally in the first embodiment $R_8$ and/or $R_9$ is —$CH_2$-secondary amine.

In an alternative preferred embodiment $R^1$ is 12-methylmyristoyl, $R_1$ and $R_3$ are independently —OH, —CN, —$CH_2NH_2$, —$N_3$, aryl, substituted aryl, a heterocyclyl or a substituted heterocyclyl, having the heterocyclyl in each case 1–3 of the same or different heteroatoms, aminoalkylamino, or mono or di-substituted linear or cyclic aminoalkylamino, $R_2$ and $R_4$ are both —OH, $R_5$ and $R_7$ are both —$CH_3$, $R_6$ is —H, and $R_8$ and $R_9$ are both —H.

The compounds provided by this invention are semisynthetic cyclic hexapeptides derived from cyclic peptides, which are produced by culturing various microorganisms. A number of cyclic peptides are known in the literature, including mulundocandin, sporiofungin, echinocandin B and aculeacin.

These cyclic hexapeptides have closely related structures with some modification of the cyclic peptide and/or the N-acyl fatty acid chain. For example mulundocandin has a methyl-myristoyl side chain, aculeacin A has a palmitoyl side chain, echinocandin B has a linoleoyl side chain and pneumocandin Ao has a di-methylmyristoyl side chain. The naturally occurring cyclic hexapeptides of the echinocandin class have a labile C—O bond and C—N bond at the ornithine-5 position as disclosed in U.S. Pat. No. 5,378,804 issued Jan. 3, 1995.

According to the present invention there are further provided processes for the preparation of novel cyclohexapeptide compounds of general formula I above.

The invention is described herein using the terms defined below unless otherwise specified.

Throughout the specification and appended claims, a given chemical formula or name shall encompass all optical and stereoisomers as well as racemic mixtures where such isomers and mixtures exist.

As used herein, the term "$C_1$–$C_{12}$ alkyl" refers to a straight or branched alkyl chain having from one to twelve carbon atoms. Typical $C_1$–$C_{12}$ alkyl groups include methyl, ethyl, propyl, isopropyl, butyl, t-butyl, pentyl, hexyl, octyl, nonyl, decyl, undecyl, dodecyl and the like. The term "$C_1$–$C_{12}$ alkyl" includes within its definition the term "$C_1$–$C_6$ alkyl".

The term "$C_9$–$C_{20}$ alkyl" refers to a straight or branched alkyl chain having from nine to twenty carbon atoms.

The term "$C_1$–$C_{12}$ alkenyl" refers to a straight or branched chain hydrocarbon having from one to twelve carbon atoms, with at least one unsaturation. Typical alkenyl groups are groups such as vinyl, 1-propen-2-yl, 1-buten-4-yl, 2-buten-4-yl and 1-penten-5-yl.

The term "$C_9$–$C_{20}$ alkenyl" refers to a straight or branched alkyl chain having from nine to twenty carbon atoms with at least one saturation.

The term "$C_9$–$C_{20}$ alkoxy" refers to a straight or branched alkyl chain having from nine to twenty carbon atoms attached to an oxygen atom. Typical $C_9$–$C_{20}$ alkoxy groups are, for example, decyloxy, and dodecyloxy.

The term "substituted alkyl" refers to alkyl groups which may be substituted with up to three substituent groups at any available point of attachment.

The term "cycloalkyl" refers to a species of alkyl containing from 3 to 15 carbon atoms without altering or resonating double bonds between carbon atoms.

The term "aryl" refers to, for example, a phenyl which is optionally substituted by one or more substituents such as halogen, alkyl, alkoxy or nitro.

The term "fused aryl" refers to a bicyclic or polycyclic ring system such as benzene ring having any two adjacent carbon atoms in common. Typical examples of fused aryl groups are naphthalene and anthracene.

The term "heteroatom" refers to N, O, S, and P.

The term "heterocyclic" refers to a 3, 5, 6 or 7 membered ring having 1 to 3 hetero atoms which may be nitrogen, oxygen or sulphur, including pyrrolyl, pyrrolidinyl, pyridonyl, pyridyl, pyrimidyl, pyrazolyl, imidazolyl, isoxazolyl, furyl, thienyl, oxazolyl, thiazolyl, piperidyl, morphinyl, oxazolidinyl, thiazolidinyl, pyrazolidinyl, imidazolidinyl and piperazinyl.

The term "hydroxyprotecting group" refers to a substituent of an hydroxy group that is commonly employed to block or protect the hydroxy functionality while reactions are carried out on the other functional groups on the compound. Examples of such hydroxy protecting groups include tetrahydropyranyl, methoxymethyl, methylthiomethyl, t-butyl, t-amyl, trityl, benzyl, allyl, trimethylsillyl and (t-butyl) dimethylsilyl. The species of hydroxy protecting group is not critical so long as the derivatized hydroxy group is stable to the conditions of the subsequent reaction(s) and can be removed at the appropriate point without disrupting the remainder of the molecule. Preferred hydroxy protecting groups are benzyl and methyl. The term "protected hydroxy" refers to a hydroxy group bonded to one of the above hydroxy protecting groups.

Further examples of hydroxy protecting groups are described in T. W. Greene, "Protective Groups in Organic Synthesis" John Wiley and Sons, New York, N.Y. (2nd edition, 1991) Chapters 2 and 3.

One process for the preparation of cyclohexapeptide compounds of the general formula I above according to the present invention comprises:

a) reacting a cyclohexapeptide compound of the general formula I above, wherein $R^1$, $R_2$, $R_4$, $R_5$, $R_6$ and $R_7$ are as defined above in the general formula I, $R_1$ and $R_3$ are both —OH, and $R_8$ and $R_9$ are —H (compound II), with an alcohol in the presence of an acid in an aprotic solvent at a temperature ranging from 0° C. to 60° to obtain the corresponding cyclohexapeptide derivative of the formula I wherein $R^1$, $R_2$, $R_4$, $R_5$, $R_6$ and $R_7$ are as defined in the general formula I, $R_1$ and $R_3$ are —OH or —OR, such that at least one of $R_1$ or $R_3$ is —OR, wherein R is $C_1$–$C_{12}$ alkyl, $C_2$–$C_{12}$ alkenyl, fused aryl, substituted aryl, a heterocyclyl containing 1–3 heteroatoms, mono or di-substituted aminoalkyl, or a hydroxy protecting group, and $R_8$ and $R_9$ are —H (compound III);

b) reacting the compound III obtained in step (a) with an appropriate secondary amine in the presence of paraformaldehyde in an aprotic solvent at a temperature ranging from 60° C. to 150° C. to yield the desired compound of formula I, isolating and purifying the resulting compound of formula I from the reaction mixture in a known manner and if desired, converting the compound of formula I into its pharmaceutically acceptable salt in a known manner.

The final compounds of formula I can be purified by procedure well known in the art such as crystallization followed by filtration. Alternatively the solvent can be removed by extraction, evaporation and the intermediates can be purified if required by chromatography with solid support such as silica gel, alumina, RP-8 or RP-18.

The described process for the preparation of the cyclohexapeptide compound of general formula I is illustrated as follows:

SCHEME 1

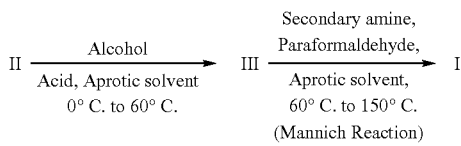

(Mannich Reaction)

The reaction of step (b) wherein the intermediate compounds III are reacted with a secondary amine in the presence of paraformaldehyde is known in the art as a Mannich Reaction.

The starting compounds II may be natural products such as mulundocandin, echinocandin B, aculeacin, pneumocandin Ao, pneumocandin Bo, pneumocandin Co and cilofungin.

In the process of the present invention, the alcohol used in step (a) may be an alkyl alcohol such as methanol or an aryl alcohol such as benzyl alcohol.

For step (a), suitable acids include strong organic acid such as trifluoroacetic acid, p-toluene sulphonic acid, camphor sulphonic acid or a lewis acid such as borontrifluoride etherate, titanium tetrachloride.

Suitable aprotic solvents used in steps (a) and (b) are selected from 1,4-dioxane, N,N-dimethylformamide(DMF), dimethylsulfoxide(DMSO), tetrahydrofuran(THF), toluene. The preferred one is 1,4-dioxane.

In step (b), the said secondary amines include compounds in which the nitrogen contains the same or different $C_1$–$C_{12}$ alkyl, $C_2$–$C_{12}$ alkenyl, aryl, substituted aryl, alkylaryl, substituted alkylaryl groups, and compounds in which the nitrogen atom of the secondary amine may be a part of a heterocyclic or substituted heterocyclic or fused heterocyclic. The heterocyclics may contain 1–3 of the same or different heteroatoms. Substituted heterocyclics may contain substituent(s) such as $C_1$–$C_6$ alkyl, $C_1$–$C_6$ alkenyl, aryl, amino, nitro and/or halogens.

Some representative examples of secondary amines are listed below: piperidine, pyrrolidine, 4-methylpiperidine, morpholine, dimethylamine, diisopropylamie, 4-piperidinopiperidine, piperazine, 1-methylpiperazine, 1-(2-fluorophenyl)piperazine, 1-(2-chlorophenyl)piperazine, 1-(2-pyrimidyl)piperazine, 1-(4-fluorophenyl)piperazine, N-(α,α,α-trifluoro-m-tolyl)piperazine, 1-phenylpiperazine, 1-benzylpiperazine, 1-(2-pyridyl)piperazine, 1-(4-pyridyl)piperazine, 1-(4-methylphenyl) piperazine, 1-(2,6-dimethylphenyl)piperazine, 1-(1-phenylethyl)piperazine, dibenzylamine, N-(tert-butyl)benzylamine and N-(isopropyl)benzylamine.

The present invention provides a second process for the preparation of compounds of the general formula I comprising:

a) reacting mulundocandin of the following formula IV,

IV

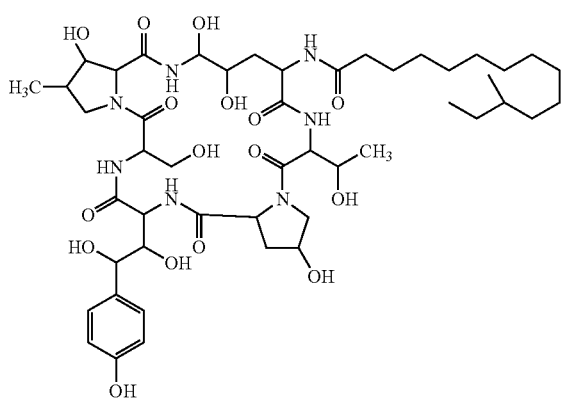

with a nucleophile such as a thiol or a thioether in presence of an acid in an aprotic solvent at a temperature ranging from 0° C. to 60° to obtain the corresponding cyclohexapeptide derivatives of formula V;

V

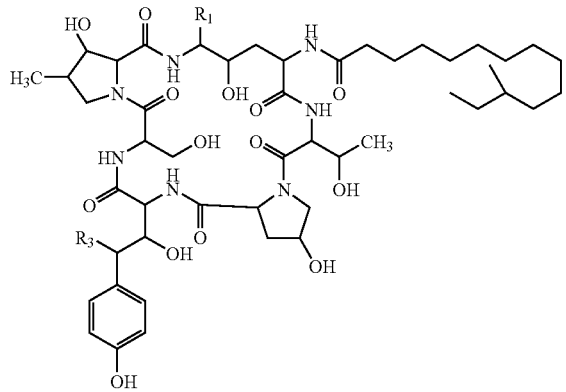

wherein $R_1$ and $R_3$ are independently —OH or —SR such that at least one of $R_1$ or $R_3$ is —SR, wherein R is $C_1$–$C_{12}$ alkyl, substituted alkyl of the type —$(CH_2)_n$—X, wherein n is 1–5 and X is Cl, Br, I, COOY, CN, $NH_2$, or a heterocyclic and Y is a $C_1$–$C_6$ linear or branched alkyl; $C_2$–$C_{12}$ alkenyl; aryl; fused aryl; substituted aryl; heterocyclyl containing 1–3 heteroatoms; mono or di-substituted aminoalkyl; or a hydroxy protecting group;

b) reacting the compounds of formula V as obtained in step (a) with an oxidising agent in an aqueous medium at a temperature ranging from 20° C. to 60° C. to obtain the corresponding sulfones of the formula VI, wherein in formula V above $R_1$ and $R_3$ are independently —OH or —S($O_2$)R, such that at least one of $R_1$ or $R_3$ is —$SO_2$R, wherein R is a $C_1$–$C_{12}$ alkyl, substituted alkyl of the type —$(CH_2)_n$—X, wherein n is 1–5 and X is Cl, Br, I, COOY, CN, $NH_2$, a heterocyclic, Y is a $C_1$–$C_6$ linear or branched alkyl chain; $C_2$–$C_{12}$ alkenyl; aryl; fused aryl; substituted aryl; heteroaryl containing 1–3 heteroatoms; heterocyclyl containing 1–3 heteroatoms; mono or di-substituted aminoalkyl; or a hydroxy protecting group;

c) reacting the sulfone (VI) obtained in step (b) with an appropriate nucleophile such as a carbon or nitrogen nucleophile in an appropriate solvent at a temperature ranging from 20° C. to 60° C. to obtain the desired compound of the formula I, isolating and purifying the resulting compound of the formula I from the reaction mixture in a known matter and, if desired, converting the compound of formula I into its pharmaceutically acceptable salt in a known manner The final compound of formula I can be purified by procedure well known in the art such as crystallisation followed by filtration. Alternatively the solvent can be removed by extraction, evaporation and the intermediate can be purified if required by chromatography with solid support such as silica gel, alumina, RP-8 or RP-18.

The process for the preparation of the cyclohexapeptide compounds of general formula I is illustrated as follows:

SCHEME 2

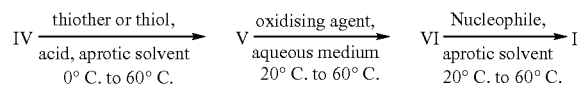

The starting, compound, Mulundocandin, is a naturally occurring cyclic lipopeptide, which is isolated from the cultured broth of a strain of *Aspergillus sydowi*, a microorganism (Indian Patent No. 162032; The Journal of Antibiotics, Vol. XL No. 3, 275–277). Mulundocandin is useful as an antibiotic.

In the process of the present invention the said nucleophile used in step (a) may be a thioether such as methylthioglycolate or an aryl thiol such as thiophenol.

Step (a) is carried out in presence of an acid which may be a strong organic acid such as trifluoroacetic acid, p-toluene sulphonic acid, camphor sulphonic acid or a lewis acid such as boron trifluoride etherate, titanium tetrachloride.

Suitable aprotic solvents used in steps (a) and (c) are selected from 1,4-dioxane, N, N-dimethylformamide (DMF), dimethylsulfoxide(DMSO), tetrahydrofuran(THF) and toluene. The preferred one is 1,4-dioxane.

In step (b), the suitable oxidising agent includes OXONE® ($KHSO_5 \cdot KHSO_4 \cdot K_2SO4:2:1:1$; obtained from Aldrich Chemicals), hydrogen peroxide and metachloroperbenzoic acid. The preferrred one is OXONE®.

The said aqueous medium used in the oxidation step is usually a mixture of solvents consisting of water and a water soluble organic solvent such as acetonitrile, dimethylformamide, dimethylsulfoxide and tetrahydrofuran. About 1:1 v/v mixture of the solvents is preferred. The preferred water soluble organic solvent is acetonitrile.

In step (c), the said nucleophile includes a carbon nucleophile or a nitrogen nucleophile.

The carbon nucleophile may be a cyanide such as sodium cyanide, potassium cyanide and lithium cyanide.

The nitrogen nucleophile may be selected from an amine, azide, heterocyclyl, substituted heterocyclyl (containing 1–3 of the same or different heteroatoms), and aminoalkylamino compounds.

In the second process of the present invention the nucleophilic substitution may take place either at ornithine-5 position only or at both the ornithine-5 and homotyrosine-4 positions depending on the intermediates formed in step (a).

The preferred representatives of cyclohexapeptide compounds of formula I' below are listed in the following Table I.

(Compounds 6-47)

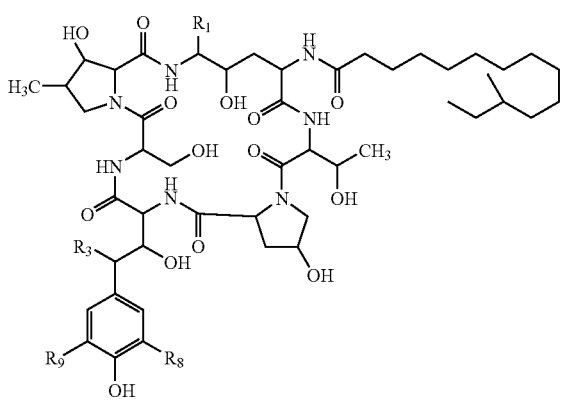

Formula I¹

TABLE I

| COMPD NO | $R_1$ | $R_3$ | $R_8$ | $R_9$ |
|---|---|---|---|---|
| 6 | —OCH₂Ph | —OH | —H₂C—N(piperidine) | —H |
| 7 | —OCH₂Ph | —OH | —H₂C—N(pyrrolidine) | —H |
| 8 | —OCH₂Ph | —OH | —H₂C—N(pyrrolidine) | —H₂C—N(pyrrolidine) |
| 9 | —OCH₂Ph | —OH | —H₂C—N(piperazine)-N-(2-F-phenyl) | —H |
| 10 | —OCH₂Ph | —OH | —H₂C—N(piperazine)-N-(2-F-phenyl) | —H₂C—N(piperazine)-N-(2-F-phenyl) |

TABLE I-continued

| COMPD NO | R₁ | R₃ | R₈ | R₉ |
|---|---|---|---|---|
| 11 | —OCH₂Ph | —OH | —H₂C-N(piperazine)N-(2-chlorophenyl) | —H |
| 12 | —OCH₂Ph | —OH | —H₂C-N(piperazine)N-(2-chlorophenyl) | —H₂C-N(piperazine)N-(2-chlorophenyl) |
| 13 | —OCH₂Ph | —OH | —H₂C-N(piperazine)N-(3-trifluoromethylphenyl) | —H |
| 14 | —OCH₂Ph | —OH | —H₂C-N(piperazine)N-(pyrimidin-2-yl) | —H |
| 15 | —OCH₂Ph | —OH | —H₂C-N(piperazine)N-(pyrimidin-2-yl) | —H₂C-N(piperazine)N-(pyrimidin-2-yl) |
| 16 | —OCH₂Ph | —OH | —H₂C-N(piperazine)N-(4-fluorophenyl) | —H |
| 17 | —OCH₂Ph | —OH | —H₂C-N(piperazine)N-(4-fluorophenyl) | —H₂C-N(piperazine)N-(4-fluorophenyl) |
| 18 | —OCH₂Ph | —OH | —H₂C-N(piperazine)N-phenyl | —H |
| 19 | —OCH₂Ph | —OH | —H₂C-N(piperazine)N-phenyl | —H₂C-N(piperazine)N-phenyl |
| 20 | —OCH₂Ph | —OH | —CH₂N(CH₂Ph)₂ | —H |
| 21 | —OCH₂Ph | —OH | —H₂C-N(piperazine)N-benzyl | —H |
| 22 | —OCH₂Ph | —OH | —H₂C-N(piperazine)N-(pyridin-2-yl) | —H |
| 23 | —OCH₂Ph | —OH | —H₂C-N(piperazine)N-(4-methylphenyl) | —H |
| 24 | —OCH₂Ph | —OH | —H₂C-N(piperazine)N-(4-methylphenyl) | —H₂C-N(piperazine)N-(4-methylphenyl) |

TABLE I-continued

| COMPD NO | R₁ | R₃ | R₈ | R₉ |
|---|---|---|---|---|
| 25 | —OCH₂Ph | —OH | —H₂C—N(piperazine)N—(4-pyridyl) | —H₂C—N(piperazine)N—(4-pyridyl) |
| 26 | —OCH₂Ph | —OH | —H₂C—N(piperazine)N—(piperidine) | —H |
| 27 | —OCH₂Ph | —OH | —H₂C—N(piperazine)N—(2,6-dimethylphenyl) | —H |
| 28 | —OCH₂Ph | —OH | —H₂C—N(piperazine)N—(2,6-dimethylphenyl) | —H₂C—N(piperazine)N—(2,6-dimethylphenyl) |
| 29 | —OCH₂Ph | —OH | —H₂C—N(piperazine)N—CH(CH₃)Ph | —H |
| 30 | —OCH₂Ph | —OH | —H₂C—N(piperazine)N—CH(CH₃)Ph | —H₂C—N(piperazine)N—CH(CH₃)Ph |
| 31 | —OCH₂Ph | —OH | —H₂C—N(t-Bu)(CH₂Ph) | —H |
| 32 | —OCH₂Ph | —OH | —H₂C—N(i-Pr)(CH₂Ph) | —H |
| 33 | —OCH₂Ph | —OH | —H₂C—N(i-Pr)(CH₂Ph) | —H₂C—N(i-Pr)(CH₂Ph) |

TABLE I-continued

| COMPD NO | R₁ | R₃ | R₈ | R₉ |
|---|---|---|---|---|
| 34 | —OCH₂Ph | —OCH₂Ph | —H₂C—N(piperidinyl) | —H |
| 35 | —OCH₂Ph | —OCH₂Ph | —H₂C—N(piperidinyl) | —H₂C—N(piperidinyl) |
| 36 | —OCH₂Ph | —OCH₂Ph | —H₂C—N(pyrrolidinyl) | —H |
| 37 | —OCH₂Ph | —OCH₂Ph | —H₂C—N(pyrrolidinyl) | —H₂C—N(pyrrolidinyl) |
| 38 | —OCH₂Ph | —OCH₂Ph | —H₂C—N(4-methylpiperidinyl) | —H |
| 39 | —OCH₂Ph | —OCH₂Ph | —H₂C—N(4-methylpiperidinyl) | —H₂C—N(4-methylpiperidinyl) |
| 40 | —OCH₂Ph | —OCH₂Ph | —H₂C—N(piperazinyl)-(3-CF₃-phenyl) | —H |
| 41 | —OCH₂Ph | —OCH₂Ph | —H₂C—N(piperazinyl)-(3-CF₃-phenyl) | —H₂C—N(piperazinyl)-(3-CF₃-phenyl) |
| 42 | —OCH₂Ph | —OCH₂Ph | —CH₂N(CH₂Ph)₂ | —H |
| 43 | —OCH₃ | —OH | —H₂C—N(piperazinyl)-(4-F-phenyl) | —H |
| 44 | —OCH₃ | —OH | —H₂C—N(piperazinyl)-(4-F-phenyl) | —H₂C—N(piperazinyl)-(4-F-phenyl) |
| 45 | —OCH₃ | —OH | —H₂C—N(piperazinyl)-phenyl | —H |
| 46 | —OCH₃ | —OH | —H₂C—N(piperazinyl)-phenyl | —H₂C—N(piperazinyl)-phenyl |
| 47 | —OCH₂OH | —N(imidazolyl) | —H₂C—N(imidazolyl) | H |

The compounds (6–47) listed in the Table 1 are prepared from Mulundocandin (Formula IV above, compound 1) as the starting material whereby in the general formula I R¹ is 12-methylmyristoyl; $R_1$, $R_2$, $R_3$ and $R_4$ each represent —OH, $R_5$ and $R_7$ each represents —CH₃, $R_6$ represents —H and $R_8$ and $R_9$ are —H.

The preferred representatives of intermediate compounds III are compounds 2–5 as described in the experimental section of the specification.

The further preferred representative compounds given in Table II have the general formula $I^1$ above in which $R^8$ and $R^9$ are H and $R_1$ and $R_3$ are the groups shown in the Table.

TABLE II

| COMPD NO | $R_1$ | $R_3$ |
|---|---|---|
| 54 | CN | —OH |
| 55 | $CH_2NH_2$ | —OH |
| 56 | HN–CH₂CH₂–N(morpholine) | —OH |
| 57 | N-imidazolyl | —OH |
| 58 | CN | CN |
| 59 | $N_3$ | $N_3$ |
| 60 | HN–CH₂CH₂–N(morpholine) | HN–CH₂CH₂–N(morpholine) |

The preferred representatives of intermediate compounds of general formula V and VI are compounds 49–53 as described in the experimental section of the specification.

The compound 55 as shown in Table II is obtained by reduction of compound 54 with a reducing agent such as $CoCl_2$—$NaBH_4$ or by hydrogenation using raney nickel as a catalyst in presence of ammonia in alcoholic solvent.

The compounds of general formula I, if desired may be converted into their pharmaceutically acceptable salts.

Preferred pharmaceutically acceptable acid addition salts are those formed with mineral acid such as hydrochloric acid and those formed with organic acid such as acetic acid.

The compounds of present invention are soluble in lower alcohols and polar aprotic solvents such as N,N-dimethylformamide (DMF), dimethyl sulfoxide (DMSO) and pyridine.

The compounds of present invention are useful for the control of both filamentous fungi and yeast. They are especially adaptable to be employed for the treatment of mycotic infections in mammals, especially those caused by *Candida* species such as *C. albicans, C.tropicals* and *C.neoforma* and *Aspergillus* species such as *A. fumigatus, A. flavus* and *A. niger*. These type of infections are usually found in immunocompromised patients such as those suffering from AIDS.

The compounds of formula I of the present invention and pharmaceutically acceptable salts thereof may be administered orally, intramuscularly, intravenously or by other modes of administration. Pharmaceutical compositions which contain the compound according to the invention or a pharmaceutically acceptable salt or derivative thereof singly or in combinations can be prepared according to standard techniques by mixing the compound(s) with one or more pharmacologically acceptable excipients and/or auxiliaries such as fillers, emulsifiers, lubricants, masking flavours colorants or buffer substances, and converting the mixture into a suitable pharmaceutical form such as tablets, coated tablets, capsules or a suspension or solution suitable for enteral or parental administration. Further details of the production of suitable pharmaceuticals may be obtained from the literature which relates to the echinocandin type of antibiotics.

As cusomary, the galenic formulation and the method of administration as well as the dosage range which are suitable in a specific case depend on the species to be treated and on the state of the respective condition or disease, and can be optimized using methods known in the art. On an average, the daily dose of a compound of the formula I in a patient of about 75 kg weight is at least 0.001 mg to at most 10 mg, preferably at most 1.0 mg.

The compounds disclosed herein have basic amino-functionality at the ornithine/homotyrosine unit(s), imparting solubility of compounds through their salts.

The following examples illustrate the invention but are not to be considered as limiting the scope of the invention.

The terms infrared spectra, electron spray ionization mass spectra, proton nuclear magnetic resonance spectra, $^{13}C$-nuclear magnetic resonance spectra, melting point, ultraviolet spectra, thin layer chromatography, high pressure liquid chromatography are abbreviated "IR", "ESI MS", "$^1$H NMR", "$^{13}C$ NMR", "m.p.", "UV", "TLC", "HPLC" respectively.

In conjunction with the $^1$H NMR spectra, the following abbreviations are used: "s" is singlet, "d" is doublet, "t" is triplet, "q" is quartet, "dd" is doublet of doublet, "br" is broad, "br.s" is broad singlet, "br.d" is broad doublet, "br.t" is broad triplet, "br.m" is broad multiplet, "J" indicates the coupling constant in Hertz (hz). $^1$H NMR, $^{13}C$ NMR, IR, MS, HPLC, m.p. data refers to the free base of the subject compound, unless otherwise mentioned.

Melting points were recorded on a Kofler hot-plate apparatus and are uncorrected. IR spectra were obtained on a Perkin-Elmer 157 spectrophotometer using KBr pellets. $^1$H NMR were recorded on a Brucker ACP-300 MHz instrument using $CD_3OD$ as solvent, unless otherwise mentioned. The chemical shifts are expressed in delta (δ) values (parts per million downfield from tetramethylsilane). $^{13}C$ NMR were recorded on a Brucker ACP-300 and the chemical shifts are expressed in ppm. Electron spray ionization mass spectra (ESI MS) were recorded on a VG QUATTRO II instrument. Perkin Elmer 235 HPLC were used for purification (Semipreparative column-Knauer Eurosphere 100, C-18 column, 250×16 mm, 10 μm, λ=220 & 270 nm) and for checking purity (Analytical column—YMC-Pack, AQ-313 S-5 120A ODS, C-18 column, 6×250 mm, 5 μm, λ=220 & 270 nm) of the compounds, according to the invention.

Procedure for the Preparation of Compounds 2 & 3:—

To a stirred solution of mulundocandin 1 (5.2 g, 5.15 mmol) in anhydrous 1,4-dioxane (150 ml), under nitrogen atmosphere was added anhydrous benzyl alcohol (10.45 g, 96.6 mmol), and a catalytic amount of p-toluenesulfonic acid (0.32 g, 1.66 mmol) and the resulting reaction mixture was stirred at ambient temperature for 1 hr. Reaction progress was monitored by TLC (20% MeOH/$CHCl_3$). TLC analysis after 1 hr. showed no starting compound. The reaction was quenched at 5–10° C. by the addition of saturated aqueous $NaHCO_3$ and evaporated to smaller volume (25 ml). The above mixture was diluted with water (250 ml), extracted with n-butanol(3×150 ml) and washed with water (200 ml) followed by brine (200 ml). Combined organic extract was dried over anhydrous $Na_2SO_4$, filtered and concentrated in vacuum to give crude gummy product, which was then dissolved in a minimum amount of methanol (15 ml), adsorbed on silica gel (1:1 w/w), and was subjected to silica gel flash column chromatography. 0–15% MeOH/CHCl$_3$ was used as 5% step gradient elution. Evaporation of the appropriate fractions gave white compound 2 (3.8 g, 67.13%) and 3 (0.82 g, 13.37%).

Compound 2:

N1-[(6S,9S,14aS,15S,16S,20S,23S,25aS,2R,11R)-12-benzyloxy-23-((1S)-2-benzyloxy-1-hydroxy-2-(4-hydroxyphenyl)ethyl)-2,11,15-trihydroxy-6-((1R)-1-hydroxyethyl)-20-hydroxymethyl-16-methyl-5,8,14,19,22,25-hexaoxo-perhydrodiazolo[2,1-c:2,1-/][1,4,7,10,13,16]hexaazacyclohenicosin-9-yl]-12-methyltetradecanamide.

Partial $^1$H NMR: 7.28–7.41 (m, 5H, OCH$_2$Ph), 7.17 (d, 2H, 8.37 Hz., Ar—H), 6.78 (d, 2H, 8.37 hz., Ar—H), 4.68 (s, 2H, OCH$_2$Ph)

$^{13}$C NMR spectrum of ornithine5-benzylmulundocandin (in DMSO-d$_6$): 172.07, 171.51, 170.46, 170.27, 169.59, 168.14, 156.57, 138.78, 132.47, 128.19, 127.94, 127.35, 127.08, 114.65, 79.01, 75.19, 74.24, 73.19, 69.23, 68.99, 68.66, 68.04, 66.10, 62.27, 60.82, 56.29, 55.67, 53.49, 51.84, 51.28, 49.23, 37.26, 36.99, 35.99, 35.13, 34.72, 33.73, 29.36, 29.03, 28.90, 28.52, 26.45, 25.42, 19.38, 19.06, 11.19, 10.81.

IR(KBr): 3350–3450 br, 2930, 1650 br, 1615, 1520, 1450, 1385(sharp), 1220, 1070 cm$^{-1}$.

ESI MS(ES+): for C$_{55}$H$_{83}$N$_7$O$_{16}$

Calculated: 1098.292

Found: (M+Na)$^+$=1120.7 (base peak), 567.4.

UV(MeOH): $\lambda_{max}$: 206, 225, 277 nm ($\epsilon$=31040, 14016, 1595)

Compound 3:

N1-[(6S,9S,14aS,15S,16S,20S,23S,25aS,2R,11R)-12-benzyloxy-23-((1S)-2-benzyloxy-1-hydroxy-2-(4-hydroxyphenyl)ethyl)-2,11,15-trihydroxy-6-((1R)-1-hydroxyethyl)-20-hydroxy-methyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.24–7.31 (m, 5H, 2×OCH$_2$Ph), 7.12 (d, 2H, 8.55 Hz., Ar—H), 6.74 (d, 2H, 8.55 hz., Ar—H), 4.4–4.53 (2×s, 4H, 2×OCH$_2$Ph)

IR(KBr):—3350–3450 br, 2930, 1650 br, 1615, 1520, 1450, 1385(sharp), 1220, 1070 cm$^{-1}$.

ESI MS(ES+): for C$_{62}$H$_{89}$N$_7$O$_{16}$

Calculated: 1188.416

Found: (M+Na)$^+$=1210.3(base peak), 1146.2, 567.4.

UV(MeOH): $\lambda_{max}$: 209, 228, 275 nm ($\epsilon$=30025, 14113, 1767)

Procedure for the Preparation of Compounds 4 & 5:—

To a stirred solution of mulundocandin 1 (2.2 g, 2.18 mmol) in anhydrous 1,4-dioxane (50 ml), under nitrogen atmosphere was added anhydrous methanol (6.0 ml, 147.9 mmol), and a catalytic amount of p-toluenesulfonic acid (0.12 g, 0.624 mmol) and the resulting reaction mixture was stirred at ambient temperature for 0.5 hr. Reaction progress was monitored by TLC (20% MeOH/CHCl$_3$). The reaction workup and purification process are similar to that described for compounds 2 and 3. Evaporation of the appropriate fractions gave white compound 4 (1.55 g, 69.53%) and 5 (0.109 g, 4.82%).

Compound 4:

N1-[(6S,9S,14aS,15S,16S,20S,23S,25aS,2R,11R)-23-((1S,2S)-1,2-dihydroxy-2-(4-hydroxy phenyl)ethyl)-2,11,15-trihydroxy-6-((1R)-1-hydroxyethyl)-20-hydroxy-methyl-12-methoxy-16-methyl-5,8,14,19,22,25-hexaoxoperhydrodiazolo-[2,1-c:2,1-/][1,4,7,10,13,16]hexaazacyclo-henicosin-9-yl]-12-methyltetradecan-amide.

Partial $^1$H NMR: 7.19 (d, 2H, 8.55 hz), 6.89 (d, 2H, 8.55 hz), 5.12 (d, 1H, 1.65 hz), 3.38 (s, 3H, OCH$_3$).

IR(KBr):—3300–3400 br, 2920, 1660 br, 1625, 1515, 1440, 1385, 1230, 1070 cm$^{-1}$

ESI MS(ES+): for C$_{49}$H$_{79}$N$_7$O$_{16}$

Calculated: 1022.194

Found: (M+Na)$^+$=1044.5 (base peak) 1030.4, 1013.4, 1000.5, 892.5, 567.3

UV(MeOH): $\lambda_{max}$: 206, 223, 277 nm ($\epsilon$=12258, 8085, 557)

Compound 5:

N1-[(6S,9S,14aS,15S,16S,20S,23S,25aS,2R,11R)-23-((1S)-1-hydroxy-2-(4-hydroxyphenyl)-2-methoxyethyl)-2,11,15-trihydroxy-6-((1R)-1-hydroxyethyl)-20-hydroxymethyl-12-methoxy-16-methyl-5,8,14,19,22,25-hexaoxoperhydrodiazolo-[2,1-c:2,1-/][1,4,7,10,13,16]hexaazacyclohe-nicosin-9-yl]-12-methyltetradecanamide.

Partial $^1$H NMR: 7.25, 7.15 (2×d, 2H, 8.37 hz), 6.82 (2×d(merged), 2H, 8.37 hz), 5.12 (br, 1H), 3.42 (2×s, 6H, 2×OCH$_3$).

IR(KBr): 3300–3400 br, 2915, 1650 br, 1630, 1520, 1445, 1390(sharp),1240, 1080 cm$^{-1}$ ESI MS(ES+): for C$_{50}$H$_{81}$N$_7$O$_{16}$ Calculated: 1036.221

Found: (M+Na)$^+$=1058.6 (base peak) 1014.5, 840.5, 567.2.

UV(MeOH): $\lambda_{max}$: 205, 223, 275 nm ($\epsilon$=1514, 5526, 506)

Compound 6:

N1-[(6S,9S,14aS,15S,16S,20S,23S,25aS,2R,11R)-23-((1S,2S)-2-(3-(1-azinanyl-methyl)-4-hydroxyphenyl)-1,2-dihydroxyethyl)-12-benzyloxy-2,11,15-trihydroxy-6-((1R)-1-hydroxy-ethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

In a 25 ml oven dried round-bottom flask were placed ornithine-5-benzylmulundocandin 2 (0.1 g, 0.091 mmol), piperidine (0.077 g, 0.91 mmol), paraformaldehyde (0.0546 g, 1.82 mmol), and anhydrous 1,4-dioxane (10 ml) and the ingredients were heated under reflux for 2 hr. Reaction progress was monitored by TLC (20% MeOH/CHCl$_3$). TLC analysis after 2 hr. showed no starting compound. Reaction mixture was cooled to ambient temperature, the solvent was evaporated under vacuum to leave a crude residue, which was then diluted with water (100 ml) and extracted with n-butanol (3×50 ml). The n-butanol extract was washed with water (100 ml) followed by brine (100 ml). Combined organic extract was dried over anhydrous Na$_2$SO$_4$, filtered and concentrated in vacuum to give impure product, which was then dissolved in minimum amount of methanol (5 ml), adsorbed on silica gel (1:1 w/w), and was subjected to silica gel flash column chromatography. 0–25% MeOH/CHCl$_3$ was used as 5% step gradient elution. Evaporation of the appropriate fractions gave white compound 6 (0.03 g, 27.57%).

Partial $^1$H NMR: 7.28–7.41 (m, 5H, —OCH$_2$Ph), 7.17 (dd, 1H, 8.32 hz & 1.8 hz), 7.0 (d, 1H, 1.8 hz), 6.78 (d, 1H, 8.37 hz), 5.31 (d, 1H, 1.65 hz), 4.68 (s, 2H, —OCH$_2$Ph), 4.05 (s, 2H, d), 2.7 (m, 4H), 1.45–1.7 (m, 6H).

IR(KBr): 3300–3400 br, 2920, 1660 br, 1630, 1540, 1460, 1260, 1075 cm$^{-1}$

ESI MS(ES+): for C$_{61}$H$_{94}$N$_8$O$_{16}$

Calculated: 1195.451

Found:(M+Na)$^+$=1217.5 1132.5 (base peak), 1088.4, 808.3, 567.2.

UV(MeOH): $\lambda_{max}$: 210, 232, 276 nm ($\epsilon$=60230, 33362, 4381)

General Procedure for the Preparation of Compounds 7–46:—

To a stirred solution of compound 2, 3 or 4 (1 eq.) in anhydrous 1,4-dioxane (10–40 ml) was slowly added secondary amine (10 eq.) and paraformaldehyde (20 eq.) and the ingredients were heated under reflux(100–120° C.) for 2–31 hr. Reaction progress was monitored by TLC (20% MeOH/CHCl$_3$). The reaction workup and purification process are similar to the described for compound 6. Stoichiometric ratios of starting compound, secondary amine, paraformaldehyde and anhydrous 1,4-dioxane are given in Table-III. Yield, m.p., reaction time, molecular formula and molecular weight of the compounds (7–46) are given in Table-III.

Compound 7:
N1-[(6S,9S,14aS,15S,16S,20S,23S,25aS,2R,11R)-23-((1S,2S)-2-(3-(1-azolanylmethyl)-4-hydroxyphenyl)-1,2-dihydroxyethyl)-12-benzyloxy-2,11,15-trihydroxy-6-((1R)-1-hydroxy-ethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.3–7.4 (m, 5H, OCH$_2$Ph), 7.25 (dd, 1H, 8.55 hz & 1.9 hz), 7.15 (d, 1H, 1.9 hz), 6.85 (d, 1H, 8.55 hz), 5.33 (d, 1H, 1.65 hz), 4.65 (s, 2H, —OCH$_2$Ph), 4.12 (s, 2H), 3.3 (m, 4H), 2.05 (m, 4H).

IR(KBr): 3300–3400 br, 2930, 1650, 1625, 1530, 1450, 1260, 1080 cm$^{-1}$

ESI MS(ES+): for C$_{60}$H$_{92}$N$_8$O$_{16}$
Calculated: 1181.424
Found: (M+Na)$^+$=1204.7 1132.5 (base peak),1056.5, 567.2.
UV(MeOH): $\lambda_{max}$: 207, 231, 280 nm ($\epsilon$=49807, 15214, 3515)

Compound 8:
N1-[(6S,9S,14aS,15S,16S,20S,23S,25aS,2R,11R)-12-benzyloxy-23-((1S,2S)-2-(3,5-di(1-azo-lanylmethyl)-4-hydroxyphenyl)-1,2-dihydroxyethyl)-2,11,15-trihydroxy-6-((1-R)-1-hydroxy-ethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.28–7.41 (m, 5H, OCH$_2$Ph), 7.09 (s, 2H), 5.33 (br, 1H), 4.68 (s, 2H, OCH$_2$Ph), 4.13 (s, 4H), 3.1 (m, 8H), 1.95 (m, 8H).

IR(KBr): 3300–3400 br, 2930, 1650, 1625, 1530, 1450, 1260, 1080 cm$^{-1}$

ESI MS(ES+): for C$_{65}$H$_{101}$N$_9$O$_{16}$
Calculated: 1264.557
Found: (M+Na)$^+$=1287.6 1215.5, 1144.5 (base peak), 567.1.

Compound 9:
N1-[(6S,9S,14aS,15S,16S,20S,23S,25aS,2R,11R)-12-benzyloxy-23-((1S,2S)-2-(3-(4-(2-flurophenyl)-1,4-diazinan-1-ylmethyl)-4-hydroxyphenyl)-1,2-dihydroxyethyl)-2,11,15-tri-hydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetra-decanamide.

Partial $^1$H NMR: 7.28–7.41 (m, 5H, OCH$_2$Ph), 7.17 (dd, 1H, 8.11 hz & 1.86 hz), 7.0–7.15 (m, 5H), 6.8 (d, 1H, 8.11 hz), 5.32 (d, 1H, 1.8 hz), 4.67 (s, 2H, OCH$_2$Ph), 3.85 (s, 2H), 3.18 (m, 4H), 2.82 (m, 4H).

IR(KBr): 3300–3400 br, 2910, 1640 br, 1615, 1515, 1490(sharp), 1440, 1225, 1060 cm$^{-1}$ ESI MS(ES+): for C$_{66}$H$_{96}$FN$_9$O$_{16}$
Calculated: 1290.527
Found: (M+Na)$^+$=1312.6 1290.7, 1132.6 (base peak), 1088.4, 567.0.
UV(MeOH): $\lambda_{max}$: 207, 231, 276 nm ($\epsilon$=41469, 14667, 4107)

Compound 10:
N1-[(6S,9S,14aS,15S,16S,20S,23S,25aS,2R,11R)-12-benzyloxy-23-((1S,2S)-2-(3,5-di(4-(2-flurophenyl)-1,4-diazinan-1-ylmethyl)-4-hydroxyphenyl)-1,2-dihydroxyethyl)-2,11,15-trihy-droxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.28–7.41 (m, 5H, OCH$_2$Ph), 7.16 (s, 2H), 7.0–7.15 (m, 8H), 5.32 (d, 1H, 1.8 hz), 4.67 (s, 2H, OCH$_2$Ph), 3.9 (s, 4H), 3.2 (br, 8H), 2.9 (br, 8H).

IR(KBr): 3300–3400 br, 2910, 1660 br, 1620, 1520, 1490, 1440, 1235, 1060 cm$^{-1}$

ESI MS(ES+): for C$_{77}$H$_{109}$F$_2$N$_{11}$O$_{16}$
Calculated: 1482.763
Found: (M+Na)$^+$=1504.9 1483.0, 1324.7, 1194.7, 1146.6, 567.3.
UV(MeOH): $\lambda_{max}$: 207, 235, 278 nm ($\epsilon$=40426, 11675, 2626)

Compound 11:
N1-[(6S,9S,14aS,15S,16S,20S,23S,25aS,2R,11R)-12-benzyloxy-23-((1S,2S)-2-(3-(4-(2-chlorophenyl)-1,4-diazinan-1-ylmethyl)-4-hydroxyphenyl)-1,2-dihydroxyethyl)-2,11,15-tri-hydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecana-mide.

Partial $^1$H NMR: 7.28–7.40, 7.15–7.21, 7.05–7.12 (3×m, 11H, Ar—H), 6.81 (d, 1H, 8.01 hz, Ar—H), 5.31 (d, 1H, 1.86 hz), 4.67 (s, 2H, OCH$_2$Ph), 3.88 (s, 2H), 3.18 (br, 4H), 2.9 (br, 4H).

IR(KBr): 3350–3450 br, 2935, 1650 br, 1630, 1530, 1450, 1260, 1130, 1080 cm$^{-1}$

ESI MS(ES+): for C$_{66}$H$_{96}$ClN$_9$O$_{16}$
Calculated: 1306.982
Found: (M+Na)$^+$=1329.6 1308.5, 1198.8, 132.7 (base peak).
UV(MeOH): $\lambda_{max}$: 209, 249, 276 nm ($\epsilon$=44379, 8061, 3572)

Compound 12:
N1-[(6S,9S,14aS,15S,16S,20S,23S,25aS,2R,11R)-12-benzyloxy-23-((1S,2S)-2-(3,5-di(4-(2-chlorophenyl)-1,4-diazinan-1-ylmethyl)-4-hydroxyphenyl)-1,2-dihydroxyethyl)-2,11,15-trihy-droxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.28–7.40, 7.15–7.12, 7.06–7.13 (3×m, 15H, Ar—H), 5.33 (br, 1H), 4.67 (s, 2H, OCH$_2$Ph), 3.87 (s, 4H), 3.18 (br, 8H), 2.95 (br, 8H).

IR(KBr): 3350–3450 br, 2930, 1645 br, 1630, 1530, 1450, 1260, 1130, 1075 cm$^{-1}$

ESI MS(ES+): for C$_{77}$H$_{109}$Cl$_2$N$_{11}$O$_{16}$
Calculated: 1515.672
Found: (M+Na)$^+$=1538.7 1144.3 (base peak), 567.4.

Compound 13:
N1-[(6S,9S,14aS,15S,16S,20S,23S,25aS,2R,11R)-12-benzyloxy-23-((1S,2S)-1,2-dihydroxy-2-(4-hydroxy-3-(4-(3-trifluromethylphenyl)-1,4-diazinan-1-ylmethyl)phenyl)ethyl)-2,11,15-trihy-droxy-6-((1R)-1-hydroxyethyl)-20- hydroxymethyl-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.28–7.45 (m, 5H, OCH$_2$Ph), 7.18–7.26 (m, 4H), 7.15 (dd, 1H, 8.13 hz & 1.86 hz), 7.1 (d, 1H, 1.86 hz), 6.8 (d, 1H, 8.13 hz), 5.32 (d, 1H, 1.86 hz), 4.68(s, 2H, OCH$_2$Ph), 3.8 (s, 2H), 2.85 (br, 8H).

$^{13}$C NMR Spectrum: 176.82, 174.90, 174.23, 174.09, 173.56, 172.72, 170.74, 159.17, 153.73, 153.65, 140.71, 133.76, 133.35, 133.12, 132.93, 131.67, 130.70, 130.08, 129.66, 129.39, 128.44, 124.11, 123.53, 121.13, 117.53, 113.82, 81.45, 77.57, 76.85, 76.57, 72.22, 71.04, 70.68, 69.04, 64.18, 63.26, 62.07, 60.36, 59.16, 57.88, 56.43, 54.67, 54.28, 53.64, 51.89, 39.84, 39.45, 38.56, 37.64, 36.46, 35.96, 31.89, 31.58, 31.47, 31.36, 31.11, 28.99, 27.85, 20.57, 20.46, 12.56, 12.01.

IR(KBr): 3350–3450 br, 2930, 1660 br, 1635, 1540, 1455, 1330, 1260, 1180, 1130, 1075 cm$^{-1}$

ESI MS(ES+): for $C_{67}H_{96}F_3N_9O_{16}$
Calculated: 1340.535
Found:(M+Na)$^+$=1362.6 1266.6, 1132.6 (base peak), 1024.6, 808.3, 567.0.

UV(MeOH): $\lambda_{max}$: 208, 240, 255 nm ($\epsilon$=4902, 904, 1609)

Compound 14:
N1-[(6S,9S,14aS,15S,16S,20S,23S,25aS,2R,11R)-12-benzyloxy-23-((1S,2S)-2-(3-(4-(1,3-diazin-2-yl)-1,4-diazinan-1-ylmethyl)-4-hydroxyphenyl-1,2-dihydroxyethyl)-2,11,15-trihy-droxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradeca-namide.

Partial $^1$H NMR: 8.36 (d, 2H, 7.8 hz), 7.29–7.41 (m, 5H, OCH$_2$Ph), 7.19 (dd, 1H, 8.01 hz & 1.86 hz, Ar—H), 7.08 (d, 1H, 1.86 hz, Ar—H), 6.81 (d, 1H, 8.01 hz, Ar—H), 6.65 (t, 1H, 9.3 hz & 4.5 hz, Ar—H), 5.31 (d, 1H, 1.53 hz), 4.68 (s, 2H, OCH$_2$Ph), 3.85 (s, 2H), 3.95 (br. 4H), 2.75 (br, 4H).

IR(KBr): 3350–3450 br, 2940, 1660 br, 1630, 1590(s), 1550, 1450, 1390, 1365, 1270, 1075 cm$^{-1}$

ESI MS(ES+): for $C_{64}H_{95}N_{11}O_{16}$
Calculated: 1274.512
Found:(M+Na)$^+$=1296.5 1274.8, 1167.7, 1132.7 (base peak), 1088.6, 567.3.

Compound 15:
N1-[(6S,9S,14aS,15S,16S,20S,23S,25aS,2R,11R)-12-benzyloxy-23-((1S,2S)-2-(3,5-di-(4-(1,3-diazin-2-yl)-1,4-diazinan-1-ylmethyl)-4-hydroxyphenyl-1,2-dihydroxyeth-yl)-2,11,15-trihydro-xy-6-((1R)-1-hydroxyethyl)-20-hydroxymethyl-16-methyl-5,8,14,19,22,25-hexaoxoperhydrodi-azolo[2,1-c:2,1-/][1,4,7,10,13,16]hexaazacyclohenicosin-9-yl]-12-methyltetradecanamide.

Partial $^1$H NMR: 8.35 (d, 4H, 7.8 hz, Ar—H), 7.26–7.41 (m, 5H, OCH$_2$Ph), 7.13 (s, 2H), 6.63 (t, 2H, 9.6 hz, 4.8 hz, Ar—H), 5.31 (br.s, 1H), 4.68 (s, 2H, OCH$_2$Ph), 3.9 (s, 4H), 3.95 (br. 8H), 2.75 (br., 8H).

IR(KBr): 3350–3450 br, 2925, 1660 br, 1630, 1590(s), 1550, 1450, 1390, 1360, 1265, 1080 cm$^{-1}$

ESI MS(ES+): for $C_{73}H_{107}N_{15}O_{16}$
Calculated: 1450.773
Found:(M+Na)$^+$=1472.7 1451.7, 1308.4, 1144.6(base peak), 567.2.

Compound 16:
N1-[(6S,9S,14aS,15S,16S,20S,23S,25aS,2R,11R)-12-benzyloxy-23-((1S,2S)-1,2-dihydroxy-2-(3-(4-(4-flurophenyl)-1,4-diazinan-1-ylmethyl)-4-hydroxyphenyl)ethyl)-2,11,15-trihydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.28–7.41 (m, 5H, OCH$_2$Ph), 7.18 (dd, 1H, 8.40 hz & 1.53 hz, Ar—H), 7.08 (d, 1H, 1.53 hz, Ar—H), 7.0 (d, 4H, 8.16 hz, Ar—H), 6.8 (d, 1H, 8.40 hz, Ar—H), 5.33 (d, 1H, 1.5 hz), 4.68 (s, 2H, OCH$_2$Ph), 3.85 (s, 2H), 3.20 (br., 4H), 2.80 (br., 4H).

IR(KBr): 3350–3450 br, 2920, 1645 br, 1615, 1509, 1430, 1225, 1065 cm$^{-1}$

ESI MS(ES+): for $C_{66}H_{96}FN_9O_{16}$
Calculated: 1290.527
Found:(M+Na)$^+$=1312.4 1291.7, 1182.6, 1164.7, 1132.5 (base peak), 1088, 567.1.

Compound 17:
N1-[(6S,9S,14aS,15S,16S,20S,23S,25aS,2R,11R)-12-benzyloxy-23-((1S,2S)-2-(3,5-di(4-(4-flurophenyl)-1,4-diazinan-1-ylmethyl)-4-hydroxyphenyl)-1,2-dihydroxyethyl)-2,11,15-trihydro-xy-6-((1R)-1-hydroxyethyl)-20-hydroxymethyl-16-methyl-5,8,14,19,22,25-hexaoxoperhydrodi-azolo[2,1-c:2,1-/][1,4,7,10,13,16]hexaazacyclohenicosin-9-yl]-12-methyltetradecanamide.

Partial $^1$H NMR: 7.28–7.41 (m, 5H, OCH$_2$Ph), 7.14 (s, 2H, Ar—H), 7.0 (d, 8H, 7.41 hz, Ar—H), 5.33 (d, 1H, 1.8 hz), 4.68 (s, 2H, OCH$_2$Ph), 3.85 (s, 4H), 3.22 (br, 8H), 2.83 (br, 8H).

IR(KBr): 3350–3450 br, 2920, 1645 br, 1615, 1509, 1430, 1225, 1065 cm$^{-1}$

ESI MS(ES+): for $C_{77}H_{109}F_2N_{11}O_{16}$
Calculated: 1482.763
Found:(M+Na)$^+$=1504.8 1482.9, 1225.7, 1268.6, 1195.8, 1144.7, 1088.6, 567.3.

UV(MeOH): $\lambda_{max}$: 210, 233, 285 nm ($\epsilon$=75574, 36321, 8063)

Compound 18:
N1-[(6S,9S,14aS,15S,16S,20S,23S,25aS,2R,11R)-12-benzyloxy-23-((1S,2S)-1,2-dihydroxy-2-(4-hydroxy-3-(4-phenyl)-1,4-diazinan-1-ylmethyl)phenyl)ethyl)-2,11,15-trihydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16] hexaazacyclohenicosin-9-yl]-12-methyltetradecanamide.

Partial $^1$H NMR: 7.28–7.41(m, 5H, OCH$_2$Ph), 7.21–7.27 (m, 2H, Ar—H), 7.19 (dd, 1H, 8.40 hz & 2.16 hz, Ar—H), 7.08 (d, 1H, 2.16 hz), 7.02 (d, 2H, 8.40 hz), 6.90 (t, 1H, 7.20 hz), 6.80 (d, 1H, 8.40 hz), 5.31 (d, 1H, 2.25 hz), 4.68 (s, 2H, OCH$_2$Ph), 3.85 (s, 2H), 3.27 (br, 4H), 2.80 (br, 4H,).

IR(KBr): 3300–3400 br, 2910, 1645 br, 1610, 1515, 1430, 1215, 1060 cm$^{-1}$

ESI MS(ES+): for $C_{66}H_{97}N_9O_{16}$
Calculated: 1272.537
Found:(M+Na)$^+$=1294.7 1272.4, 1132.5 (base peak), 1089.9, 808.5, 567.2.

UV(MeOH): $\lambda_{max}$: 207, 230, 246, 279 nm ($\epsilon$=47454, 14338, 12697, 3314)

Compound 19:
N1-[(6S,9S,14aS,15S,16S,20S,23S,25aS,2R,11R)-12-benzyloxy-23-((1S,2S)-1,2-dihydroxy-2-(4-hydroxy-3,5-di(4-phenyl)-1,4-diazinan-1-ylmethyl)phenyl)ethyl)-2,11,15-trihydroxy-6-((1R)-1-hydroxyethyl)-20-hydroxymethyl-16-methyl-5,8,14,19,22,25-hexaoxoperhydrodiazolo-[2,1-c:2,1-/][1,4,7,10,13,16] hexaazacyclohenicosin-9-yl]-12-methyltetradecanamide.

Partial $^1$H NMR: 7.25–7.41 (m, 9H, OCH$_2$Ph), 7.14 (s, 2H, Ar—H), 7.03 (d, 4H, 8.70 hz, Ar—H), 6.88 (tt, 2H, 7.5 hz & 1.2 hz, Ar—H), 5.31 (d, 1H, 1.53 hz), 4.68 (s, 2H, OCH$_2$Ph), 3.85 (s, 4H), 3.87 (br, 8H,), 2.80 (br, 8H).

IR(KBr): 3300–3400 br, 2910, 1650 br, 1625, 1525, 1440, 1220, 1060 cm$^{-1}$

ESI MS(ES+): for C$_{77}$H$_{111}$N$_{11}$O$_{16}$
Calculated: 1446.782
Found:(M+Na)$^+$=1468.8 1446.8, 1306.8, 1176.8, 1144.6 (base peak), 1036.7, 567.2.
UV(MeOH): λ$_{max}$: 208, 248, 282 nm (ε=65504, 32883, 4472)

Compound 20:
N1-[(6S,9S,14aS,15S,16S,20S,23S,25aS,2R,11R)-12-benzyloxy-23-((1S,2S)-2-(3-dibenzyl aminomethyl-4-hydroxyphenyl)-1,2-dihydroxyethyl)-2,11,15-trihydroxy-6-((1R)-1-hydroxy-ethyl)-20-hydroxymethyl-16-methyl-5,8,14,19,22,25-hexaoxoperhydrodiazolo[2,1-c:2,1-/][1,4,7,10,13,16] hexaazacyclohenicosin-9-yl]-12-methyltetradecanamide.

Partial $^1$H NMR: 7.28–7.42 (m, 15H, OCH$_2$Ph, 2×NCH$_2$Ph), 7.17 (dd, 1H, 8.64 hz & 2.16 hz, Ar—H), 7.09 (d, 1H, 2.16 hz, Ar—H), 6.79 (d, 1H, 8.64 hz, Ar—H), 5.31 (d, 1H, 1.53 hz), 4.68 (s, 2H, OCH$_2$Ph), 3.63–3.7 (2×s, 6H).

$^{13}$C NMR Spectrum: 176.83, 174.96, 174.15, 174.08, 173.5, 172.66, 170.62, 158.97, 140.66, 139.11, 134.0, 131.51, 130.44, 130.02, 129.76, 129.67, 129.57, 129.34, 128.86, 124.07, 117.41, 81.46, 77.39, 76.77, 76.48, 72.21, 72.12, 71.05, 70.63, 69.01, 64.09, 63.15, 59.53, 59.24, 57.88, 56.74, 56.36, 53.55, 51.99, 39.80, 39.38, 38.54, 37.60, 36.43, 35.95, 31.87, 31.55, 31.42, 31.36, 31.06, 28.96, 27.83, 20.42, 12.53, 11.98.

IR(KBr): 3300–3400 br, 2910, 1640 br, 1615, 1515, 1430, 1240, 1060 cm$^{-1}$

ESI MS(ES+): for C$_{70}$H$_{98}$N$_8$O$_{16}$
Calculated: 1307.582
Found:(M+Na)$^+$=1330.7 1132.6 (base peak), 1024.4, 567.2.
UV(MeOH): λ$_{max}$: 206, 225, 279 nm (ε=37234, 8761, 15135)

Compound 21:
N1-[(6S,9S,14aS,15S,16S,20S,23S,25aS,2R,11R)-23-((1S,2S)-2-(3-(4-benzyl-1,4-diazinan-1-ylmethyl)-4-hydroxyphenyl)-1,2-dihydroxyethyl)-12-benzyloxy-2,11,15-trihydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.28–7.43 (m, 10H, OCH$_2$Ph, —NCH$_2$Ph), 7.18 (dd, 1H, 8.64 hz & 1.86 hz, Ar—H), 7.03 (d, 1H, 1.86 hz, Ar—H), 6.78 (d, 1H, 8.64 hz, Ar—H), 5.31 (d, 1H, 2.04 hz), 4.68 (s, 2H, —OCH$_2$Ph), 3.58–3.62 (2×s, 4H), 3.18, 2.68 (2×t, 8H).

IR(KBr): 3300–3400 br, 2930, 1650 br, 1625, 1520, 1450, 1390, 1260, 1070 cm$^{-1}$

ESI MS(ES+): for C$_{67}$H$_{99}$N$_9$O$_{16}$
Calculated: 1286.563
Found:(M+Na)$^+$=1309.6 1132.5 (base peak), 1088.3, 567.2.
UV(MeOH): λ$_{max}$: 208, 229, 280 nm (ε=42242, 12359, 2648)

Compound 22:
N1-[(6S,9S,14aS,15S,16S,20S,23S,25aS,2R,11R)-23-((1S,2S)-2-(3-(4-(2-azinyl)-1,4-diaz-inan-1-ylmethyl)-4-hydroxyphenyl-1,2-dihydroxyethyl)-12-benzyloxy-2,11,15-trihydroxy-6-((1R)-1-hydroxyethyl)-20-hydroxymethyl-16-methyl-5,8,14,19,22,25-hexaoxoperhydrodi-azolo[2,1-c:2,1-/][1,4,7,10,13,16]hexaazacyclohenicosin-9-yl]-12-methyltetradecanamide.

Partial $^1$H NMR: 8.1–8.16 (m, 1H, Ar—H), 7.6 (m, 1H, Ar—H), 7.3–7.45 (m, 5H, —OCH$_2$Ph), 7.18 (dd, 1H, 8.37 hz & 1.41 hz, Ar—H), 7.08 (d, 1H, 1.41 hz, Ar—H), 6.89 (m, 1H, Ar—H), 6.8 (d, 1H, 8.37 hz, Ar—H), 6.75 (m, 1H, Ar—H), 5.31 (d, 1H, 1.53 hz), 4.68 (s, 2H, —OCH$_2$Ph), 3.8 (s, 2H), 3.6 (m, 4H), 2.72 (m, 4H).

IR(KBr): 3300–3400 br, 2930, 1640 br, 1620, 1520, 1430, 1375, 1235, 1060 cm$^{-1}$

ESI MS(ES+): for C$_{65}$H$_{96}$N$_{10}$O$_{16}$
Calculated: 1273.524
Found:(M+Na)$^+$=1295.7 1273.7, 1132.5, 808.4, 567.2.
UV(MeOH): λ$_{max}$: 208, 248, 299 nm (ε=43844, 27725, 5899)

Compound 23:
N1-[(6S,9S,14aS,15S,16S,20S,23S,25aS,2R,11R)-12-benzyloxy-23-((1S,2S)-1,2-dihydroxy-2-(4-hydroxy-3-(4-(4-methylphenyl)-1,4-diazinan-1-ylmethyl)phenyl)ethyl)-2,11,15-trihydroxy-6-((1R)-1-hydroxyethyl)-20-hydroxymethyl-16-methyl-5,8,14,19,22,25-hexaoxoperhydrodiazolo-[2,1-c:2,1-/] [1,4,7,10,13,16] hexaazacyclohenicosin-9-yl]-12-methyltetradecanamide.

Partial $^1$H NMR: 7.29–7.43 (m, 5H, —OCH$_2$Ph), 7.18 (dd, 1H, 8.64 hz & 1.53 hz), 7.06–7.12 (m, 3H, Ar—H), 6.93 (d, 2H, 8.64 hz, Ar—H), 6.79 (d, 1H, 8.64 hz, Ar—H), 5.31 (d, 1H, 1.53 hz), 4.68 (s, 2H, —OCH$_2$Ph), 3.81 (s, 2H), 3.2 (br, 4H), 2.78 (br, 4H), 2.38 (s, 3H, Ar—CH$_3$).

IR(KBr): 3300–3400 br, 2930,1640 br, 1620, 1520, 1430, 1375, 1235, 1060 cm$^{-1}$

ESI MS(ES+): for C$_{67}$H$_{99}$N$_9$O$_{16}$
Calculated: 1286.583
Found:(M+Na)$^+$=1309.6 1273.7, 1132.5, 808.4, 567.2.
UV(MeOH): λ$_{max}$: 209, 230, 247, 279 nm (ε=71176, 61764, 20808, 5147)

Compound 24:
N1-[(6S,9S,14aS,15S,16S,20S,23S,25aS,2R,11R)-12-benzyloxy-23-((1S,2S)-1,2-dihydroxy-2-(4-hydroxy-3,5-di(4-(4-methylphenyl)-1,4-diazinan-1-ylmethyl)phenyl)ethyl)-2,11,15-trihydro-xy-6-((1R)-1-hydroxyethyl)-20-hydroxymethyl-16-methyl-5,8,14,19,22,25-hexaoxoperhydrodi-azolo[2,1-c:2,1-/] [1,4,7,10,13,16] hexaazacyclohenicosin-9-yl]-12-methyltetradecanamide.

Partial $^1$H NMR: 7.29–7.43 (m, 5H, —OCH$_2$Ph), 7.14 (s, 2H), 7.1 (d, 4H, 8.64 hz), 6.92 (d, 4H, 8.64 hz), 5.33 (d, 1H, 1.86 hz), 4.68 (s, 2H, —OCH$_2$Ph), 3.82 (s, 4H), 3.21 (br, 8H), 2.73 (br, 8H), 2.29 (s, 6H, 2×Ar—CH$_3$).

IR(KBr): 3350–3450 br, 2940, 1655 br, 1630, 1519 (sharp), 1450, 1385(sharp), 1060 cm$^{-1}$ ESI MS(ES+): for C$_{79}$H$_{115}$N$_{11}$O$_{16}$
Calculated: 1474.835
Found:(M+Na)$^+$=1496.8 1474.6, 1389.1, 1320.5, 1144.4 (base peak), 1036.4, 567.4.
UV(MeOH): λ$_{max}$: 210, 242, 284 nm (ε=62037, 26909, 5900)

Compound 25:
N1-[(6S,9S,14aS,15S,16S,20S,23S,25aS,2R,11R)-12-benzyloxy-23-((1S,2S)-2-(3,5-di(4-(4-azinyl)-1,4-diazinan-1-ylmethyl)-4-hydroxyphenyl-1,2-dihydroxyethyl)-2,11,15-trihydroxy-6-((1R)-1-hydroxyethyl)-20-hydroxymethyl-16-methyl-5,8,14,19,22,25-hexaoxoperhydrodiazolo-[2,1-c:2,1-/][1,4,7,10,13,16]hexaazacyclohenicosin-9-yl]-12-methyltetradecanamide.

Partial $^1$H NMR: 8.15–8.22 (m, 4H, Ar—H), 7.25–7.43 (m, 5H, —OCH$_2$Ph), 7.14 (s, 2H, Ar—H), 7.0 (m, 4H, Ar—H), 5.31 (br, 1H), 4.68 (s, 2H, —OCH$_2$Ph), 3.81 (s, 4H), 3.65 (br, 8H), 2.73 (br, 8H).

IR(KBr): 3350–3450 br, 2920, 1650 br, 1610, 1540, 1510, 1440, 1385(sharp), 1230, 1070 cm$^{-1}$ ESI MS(ES+): for C$_{75}$H$_{109}$N$_{13}$O$_{16}$
Calculated: 1448.457
Found:(M+Na)$^+$=1470.6 1449.6, 1307.5, 1199.4, 1177.8, 1036.3.

UV(MeOH): $\lambda_{max}$: 208, 237, 262 nm ($\epsilon$=75379, 10463, 41034)

Compound 26:

N1-[(6S,9S,14aS,15S,16S,20S,23S,25aS,2R,11R)-23-((1S,2S)-2-(3-(4-(1-azinanyl)-1-azina-nylmethyl)-4-hydroxyphenyl)-1,2-dihydroxyethyl)-12-benzyloxy-2,11,15-trihydroxy-6-((1R)-1-hydroxyethyl)-20-hydroxymethyl-16-methyl-5,8,14,19,22,25-hexaoxoperhydrodiazolo[2,1-c:2,1-/] [1,4,7,10,13,16] hexaazacyclohenicosin-9-yl]-12-methyltetradecanamide.

Partial $^1$H NMR: 7.28–7.45 (m, 5H, —OCH$_2$Ph), 7.18 (dd, 1H, 8.64 hz & 1.86 hz, Ar—H), 7.06 (d, 1H, 1.86 hz, Ar—H), 6.8 (d, 1H, 8.64 hz, Ar—H), 5.02 (d, 1H, 1.86 hz), 4.68 (s, 2H, —OCH$_2$Ph), 3.78 (s, 2H), 2.89–3.28 (m, 9H), 1.7–1.9 (m, 10H).

IR(KBr): 3300–3400 br, 2940, 1660 br, 1635, 1518, 1460, 1370 br, 1075 cm$^{-1}$

ESI MS(ES+): for C$_{66}$H$_{103}$N$_9$O$_{16}$
Calculated: 1278.584
Found:(M+Na)$^+$=1300.5 1132.4 (base peak), 1102.7, 1024, 567.2.

UV(MeOH): $\lambda_{max}$: 208, 225, 279 nm ($\epsilon$=46029, 13780, 1619)

Compound 27:

N1-[(6S,9S,14aS,15S,16S,20S,23S,25aS,2R,11R)-12-benzyloxy-23-((1S,2S)-1,2-dihydroxy-2-(3-(4-(2,6-dimethylphenyl)-1,4-diazinan-1-ylmethyl)-4-hydroxyphenyl)ethyl)-2,11,15-trihydro-xy-6-((1R)-1-hydroxyethyl)-20-hydroxymethyl-16-methyl-5,8,14,19,22,25-hexaoxoperhydrodi-azolo[2,1-c:2,1-/] [1,4,7,10,13,16] hexaazacyclohenicosin-9-yl]-12-methyltetradecanamide.

Partial $^1$H NMR: 7.29–7.42 (m, 5H, —OCH$_2$Ph), 7.18 (dd, 1H, 8.55 hz & 1.32 hz, Ar—H), 7.09 (d, 1H, 1.32 hz, Ar—H), 6.9–7.03 (m, 3H, Ar—H), 6.81 (d, 1H, 8.55 hz, Ar—H), 5.31 (br, 1H), 4.68 (s, 2H, —OCH$_2$Ph), 3.91 (s, 2H), 3.2 (br, 4H), 2.82 (br, 4H), 2.38 (s, 6H, 2×Ar—CH$_3$).

$^{13}$C NMR Spectrum: 176.82, 174.95, 174.20, 174.03, 173.53, 172.67, 170.63, 159.28, 149.74, 140.71, 138.70, 133.76, 130.98, 130.84, 130.06, 129.64, 129.36, 127.85, 127.35, 122.66, 117.51, 81.42, 77.57, 76.79, 76.54, 72.22, 71.04, 70.74, 69.04, 64.16, 63.24, 62.09, 59.25, 57.91, 56.32, 55.62, 54.98, 54.73, 53.59, 51.94, 51.11, 39.81, 39.45, 38.56, 37.61, 36.46, 35.93, 31.89, 31.58, 31.47, 31.36, 31.11, 28.99, 27.85, 20.65, 20.51, 20.46, 12.56, 11.98.

IR(KBr): 3300–3400 br, 2935, 1660 br, 1625, 1530, 1450, 1385, 1260, 1070 cm$^{-1}$

ESI MS(ES+): for C$_{68}$H$_{101}$N$_9$O$_{16}$
Calculated: 1300.590
Found:(M+Na)$^+$=1322.5 1132.5 (base peak), 567.2.

UV(MeOH): $\lambda_{max}$: 208, 226, 267 nm ($\epsilon$=37979, 14394, 2709)

Compound 28:

N1-[(6S,9S,14aS,15S,16S,20S,23S,25aS,2R,11R)-12-benzyloxy-23-((1S,2S)-1,2-dihydroxy-2-(3,5-di(4-(2,6-dimethylphenyl)-1,4-diazinan-1-ylmethyl)-4-hydroxyphenyl)ethyl)-2,11,15-trihy-droxy-6-((1R)-1-hydroxyethyl)-20-hydroxymethyl-16-methyl-5,8,14,19,22,25-hexaoxoperhydrodiazolo[2,1-c:2,1-/] [1,4,7,10,13,16] hexaazacyclohenicosin-9-yl]-12-methyltetradecanamide.

Partial $^1$H NMR: 7.28–7.42 (m, 5H, —OCH$_2$Ph), 7.21 (s, 2H, Ar—H), 6.98–7.2 (m, 6H, Ar—H), 5.33 (br, 1H), 4.68 (s, 2H, —OCH$_2$Ph), 4.11 (s, 4H), 3.29 (br, 8H), 3.05 (br, 8H), 2.40 (s, 12H, 4×Ar—CH$_3$).

IR(KBr): 3350–3450 br, 2920, 1670 br, 1630, 1535, 1460, 1390(sharp), 1220, 1070 cm$^{-1}$ ESI MS(ES+): for C$_{81}$H$_{119}$N$_{11}$O$_{16}$
Calculated: 1502.889
Found:(M+Na)$^+$=1525.6 1503.7, 1334.6, 1204.6, 1144.6 (base peak), 668.4.

UV(MeOH): $\lambda_{max}$: 211, 226, 257, 282 nm ($\epsilon$=58787, 26424, 8513, 5187)

Compound 29:

N1-[(6S,9S,14aS,15S,16S,20S,23S,25aS,2R,11R)-12-benzyloxy-23-((1S,2S)-1,2-dihydroxy-2-(4-hydroxy-3-(4-(1-phenylethyl)-1,4-diazinan-1-ylmethyl)phenyl)ethyl)-2,11,15-trihydroxy-6-((1R)-1-hydroxyethyl)-20-hydroxymethyl-16-methyl-5,8,14,19,22,25-hexaoxoperhydrodiazolo-[2,1-c:2,1-/] [1,4,7,10,13,16] hexaazacyclohenicosin-9-yl]-12-methyltetradecanamide.

Partial $^1$H NMR: 7.28–7.45 (m, 10H, —OCH$_2$Ph & —CH(CH$_3$)Ph), 7.17 (dd, 1H, 8.55 hz & 1.32 hz, Ar—H), 7.03 (d, 1H, 1.32 hz, Ar—H), 6.77 (d, 1H, 8.55 hz, Ar—H), 5.31 (d, 1H, 1.98 hz), 4.68 (s, 2H, —OCH$_2$Ph), 3.75 (s, 2H), 3.8 (q, 1H, 7.89 hz), 2.6–2.79 (m, 8H), 1.45 (d, 3H, 7.89 hz).

$^{13}$C NMR Spectrum: 176.80, 174.92, 174.08, 173.50, 172.66, 170.65, 159.20, 144.93, 144.51, 140.70, 133.68, 130.41, 130.18, 130.05, 129.63, 129.34, 129.15, 129.08, 123.63, 117.41, 81.43, 77.49, 76.81, 76.55, 72.18, 72.12, 71.02, 70.66, 69.01, 67.13, 64.13, 63.19, 62.09, 59.21, 57.85, 56.43, 54.68, 54.29, 53.58, 52.38, 51.93, 51.41, 50.99, 46.62, 39.80, 39.41, 38.54, 37.60, 36.43, 35.95, 31.87, 31.55, 31.45, 31.36, 31.10, 28.96, 27.83, 20.94, 20.45, 12.56, 11.98.

IR(KBr): 3300–3400 br, 2920, 1660 br, 1625, 1530, 1455, 1390(sharp), 1260, 1070 cm$^{-1}$ ESI MS(ES+): for C$_{68}$H$_{101}$N$_9$O$_{16}$
Calculated: 1300.590
Found:(M+Na)$^+$=1323.6 1300.6, 1132.5, 808.5, 567.3.

UV(MeOH): $\lambda_{max}$: 206, 223, 279 nm ($\epsilon$=47065, 14834, 1881)

Compound 30:

N1-[(6S,9S,14aS,15S,16S,20S,23S,25aS,2R,11R)-12-benzyloxy-23-((1S,2S)-1,2-dihydroxy-2-(3,5-di(4-(1-phenylethyl)-1,4-diazinan-1-ylmethyl)-4-hydroxyphenyl)ethyl)-2,11,15-trihydroxy-6-((1R)-1-hydroxyethyl)-20-hydroxymethyl-16-methyl-5,8,14,19,22,25-hexaoxoperhydrodi-azolo[2,1-c:2,1-/] [1,4,7,10,13,16]-hexaazacyclohenicosin-9-yl]-12-methyltetradecanamide.

Partial $^1$H NMR: 7.22–7.40 (m, 15H, —OCH$_2$Ph & 2×—CH(CH$_3$)Ph), 6.84 (s, 2H, Ar—H), 5.02 (br, 1H), 4.45 (s, 2H, —OCH$_2$Ph), 3.52 (s, 4H), 3.42 (q, 2H, 7.8 hz), 2.3–2.55 (m, 16H), 1.28 (d, 6H, 7.8 hz).

IR(KBr): 3300–3450 br, 2920, 1655, 1625, 1525, 1450, 1385(sharp), 1255, 1070 cm$^{-1}$ ESI MS(ES+): for C$_{81}$H$_{119}$N$_{11}$O$_6$
Calculated: 1502.889
Found:(M+Na)$^+$=1525.7 1502.8, 1334.6, 1204.6, 1144.4, 763.5, 668.0, 567.0.

UV(MeOH): $\lambda_{max}$: 205, 219, 284 nm ($\epsilon$=50300, 7314, 1833)

Compound 31:
N1-[(6S,9S,14aS,15S,16S,20S,23S,25aS,2R,11R)-23-((1S,2S)-2-(3-benzyl(tert.butyl)amino-methyl-4-hydroxyphenyl)-1,2-dihydroxyethyl)-12-benzyloxy-2,11,15-trihydroxy-6-((1R)-1-hydroxyethyl)-20-hydroxymethyl-16-methyl-5,8,14,19,22,25-hexaoxoperhyd-rodiazolo[2,1-c:2,1-/] [1,4,7,10,13,16]hexaazacyclohenicosin-9-yl]-12-methyltetradecanamide.

Partial $^1$H NMR: 7.15–7.45 (m, 10H, —OCH$_2$Ph & —NCH$_2$Ph), 7.05 (dd, 1H, 8.37 hz & 1.41 hz, Ar—H), 6.95 (d, 1H, 1.41 hz, Ar—H), 6.55 (d, 1H, 8.37 hz, Ar—H), 5.32 (d, 1H, 2.1 hz), 4.68 (s, 2H, —OCH$_2$Ph), 4.09 (s, 2H), 3.89 (s, 2H), 1.42 (s, 9H, 3xe or —C(CH$_3$)$_3$).

IR(KBr): 3300–3400 br, 2920, 1660 br, 1625, 1525, 1440, 1375(sharp), 1250, 1070 cm$^{-1}$ ESI MS(ES+): for C$_{67}$H$_{100}$N$_8$O$_{16}$
Calculated: 1273.565
Found:(M+Na)$^+$=1296.6 1132.5 (base peak), 567.3.
UV(MeOH): $\lambda_{max}$: 210, 226, 280 nm ($\epsilon$=76304, 28418, 4257)

Compound 32:
N1-[(6S,9S,14aS,15S,16S,20S,23S,25aS,2R,11R)-23-((1S,2S)-2-(3-benzyl(isopropyl)amino-methyl-4-hydroxyphenyl)-1,2-dihydroxyethyl)-12-benzyloxy-2,11,15-trihydroxy-6-((1R)-1-hy-droxyethyl)-20-hydroxymethyl-16-methyl-5,8,14,19,22,25-hexaoxoperhyd-rodiazolo[2,1-c:2,1-/] [1,4,7,10,13,16]hexaazacyclohenicosin-9-yl]-12-methyltetradecanamide.

Partial $^1$H NMR: 7.28–7.45 (m, 10H, —OCH$_2$Ph & —NCH$_2$Ph), 7.16 (dd, 1H, 8.55 hz & 1.98 hz, Ar—H), 7.05 (d, 1H, 1.98 hz, Ar—H), 6.74 (d, 1H, 8.55 hz, Ar—H), 5.32 (br, 1H), 4.68 (s, 2H, OCH$_2$Ph), 3.9, 3.65 (2xs, 4H), 3.1 (m, 1H), 1.22 (m, 6H).

IR(KBr): 3300–3400 br, 2935, 1680–1625 br, 1540, 1450, 1385(sharp), 1260, 1075 cm$^{-1}$ ESI MS(ES+): for C$_{66}$H$_{98}$N$_8$O$_{16}$
Calculated: 1259.538
Found:(M+Na)$^+$=12.81.8 1132.4 (base peak), 567.1.
UV(MeOH): $\lambda_{max}$: 207, 231, 280 nm ($\epsilon$=58232, 10790, 2997)

Compound 33:
N1-[(6S,9S,14aS,15S,16S,20S,23S,25aS,2R,11R)-12-benzyloxy-23-((1S,2S)-2-(3,5-di(benzyl(iso-propyl)aminomethyl-4-hydroxyphenyl)-1,2-dihydroxyethyl)-2-benzyloxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

Partial $^1$H NMR: 7.28–7.43 (m, 15H, —OCH$_2$Ph & 2x—NCH$_2$Ph), 7.03 (s, 2H, Ar—H), 5.33 (br, 1H), 4.68 (s, 2H, —OCH$_2$Ph), 3.87, 3.63 (2xs, 8H), 3.0 (m, 2H), 1.2–1.3 (m, 12H).

IR(KBr): 3400–3500 br, 2945, 1680–1630 br, 1540, 1460, 1385(sharp), 1260, 1080 cm$^{-1}$ ESI MS(ES+): for C$_{77}$H$_{113}$N$_9$O$_{16}$
Calculated: 1420.784
Found:(M)$^+$=1420.9 1293.4, 1144.9(base peak), 1024.4, 996.2, 648.1.
UV(MeOH): $\lambda_{max}$ pH: 207, 227, 282 nm ($\epsilon$=67687, 10661, 1465)

Compound 34:
N1-[(6S,9S,14aS,15S,16S,20S,23S,25aS,2R,11R)-23-((1S)-2-(3-(1-azinanylmethyl)-4-hydro-xyphenyl)-2-benzyloxy-1-hydroxyethyl)-12-benzyloxy-2,11,15-trihydroxy-6-((1R)-1-hydroxy-thyl)-20-hydroxymethyl-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.25–7.41 (m, 10H, 2xOCH$_2$Ph), 7.2 (dd, 1H, 8.5 hz & 1.85 hz, Ar—H), 7.14 (d, 1H, 1.85 hz, Ar—H), 6.87 (d, 1H, 8.5 hz), 5.35 (br, 1H), 4.6 (s, 4H, 2x—OCH$_2$Ph), 4.14 (s, 2H), 3.12 (m, 4H), 2.04 (m, 6H).

IR(KBr): 3300–3400 br, 2915, 1650, 1620, 1530, 1440, 1250, 1070 cm$^{-1}$

ESI MS(ES): for C$_{68}$H$_{100}$N$_8$O$_{16}$
Calculated: 1285.576
Found: (M+Na)$^+$=1308.6(base peak), 567.3
UV(MeOH): $\lambda_{max}$: 211, 255, 288 nm ($\epsilon$=73984, 20087, 5142)

Compound 35:
N1-[(6S,9S,14aS,15S,16S,20S,23S,25aS,2R,11R)-12-benzyloxy-23-((1S)-2-benzyloxy-2-(3,5-di(1-azinanylmethyl)-4-hydroxyphenyl)-1-hydroxyethyl)-2,11,15-trihydroxy-6-(1R)-1-hydroxy-ethyl)-20-hydroxymethyl-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.28–7.45 (m, 10H, 2x—OCH$_2$Ph), 7.21 (2xs, 2H, Ar—H), 5.32 (br, 1H), 4.65 (s, 4H, 2x—OCH$_2$Ph), 4.11 (m, 4H), 2.98 (m, 8H), 1.98 (m, 12H).

IR(KBr): 3300–3400 br, 2910, 1650, 1625 br, 1530, 1440, 1250, 1070 cm$^{-1}$

ESI MS(ES+): for C$_{74}$H$_{111}$N$_9$O$_{16}$
Calculated 1382.735
Found:(M+Na)$^+$=1404.8 (base peak) 1382.6, 1320.7, 1189.4, 1081.6, 808.5, 567.3.
UV(MeOH): $\lambda_{max}$: 209, 234, 290 nm ($\epsilon$=46021, 9127, 3989)

Compound 36:
N1-[(6S,9S,14aS,15S,16S,20S,23S,25aS,2R,11R)-23-((1S)-2-(3-(1-azolanylmethyl)-4-hydro-xyphenyl)-2-benzyloxy-1-hydroxyethyl)-12-benzyloxy-2,11,15-trihydroxy-6-((1R)-1-hydroxy-ethyl)-20-hydroxymethyl-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.25–7.41 (m, 10H, 2x—OCH$_2$Ph), 7.25 (dd, 1H, 8.5 hz & 1.9 hz, Ar—H), 7.14 (d, 1H, 1.9 hz, Ar—H), 6.87 (d, 1H, 8.5 hz, Ar—H), 5.31 (br, 1H), 4.67(s, 4H, 2x—OCH$_2$Ph), 4.13 (s, 2H), 3.35 (m, 4H), 2.1 (m, 4H).

IR(KBr): 3300–3400 br, 2925, 1650, 1620, 1535, 1450, 1250, 1075 cm$^{-1}$

ESI MS(ES+): for C$_{67}$H$_{98}$N$_8$O$_{16}$
Calculated: 1271.549
Found:(M+Na)$^+$=1293.6 (base peak) 1159.0, 1114.5, 734.9.
UV(MeOH): $\lambda_{max}$: 211, 230, 278 nm ($\epsilon$=64015, 27056, 6845)

Compound 37:
N1-[(6S,9S,14aS,15S,16S,20S,23S,25aS,2R,11R)-12-benzyloxy-23-((1S)-2-benzyloxy-2-(3,5-di(1-azolanylmethyl)-4-hydroxyphenyl)-1-hydroxyethyl)-2,11,15-trihydroxy-6-((1R)-1-hydroxy ethyl)-20-hydroxymethyl-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.28–7.41 (m, 10H, 2x—OCH$_2$Ph), 7.10, 7.14 (2xs, 2H, Ar—H), 5.33 (br, 1H), 4.68 (s, 4H, 2x—OCH$_2$Ph), 4.18 (m, 4H), 3.12 (m, 8H), 2.05 (m, 8H).

IR(KBr): 3320–3420 br, 2920, 1660–1630 br, 1530, 1465, 1080 cm$^{-1}$

ESI MS(ES+): for $C_{72}H_{107}N_9O_{16}$

Calculated: 1354.682

Found:(M+Na)$^+$=1376.6 (base peak) 1354.5, 1305.6, 1175.7, 1067.5, 653.8.

UV(MeOH): $\lambda_{max}$: 208, 230, 289 nm ($\epsilon$=64738, 12888, 5155)

Compound 38:

N1-[(6S,9S,14aS,15S,16S,20S,23S,25aS,2R,11R)-12-benzyloxy-23-((1S)-2-benzyloxy-1-hyd-roxy-2-(4-hydroxy-3-(4-methyl-1-azinanylmethyl)phenyl)ethyl)-2,11,15-trihydroxy-6-((1R)-1-hydroxyethyl)-20-hydroxymethyl-16-methyl-5,8,14,19,22,25-hexaoxoperhydrodiazolo-[2,1-:2,1-/][1,4,7,10,13,16]hexaazacyclohenicosin-9-yl]-12-methyltetradecanamide.

Partial $^1$H NMR: 7.2–7.41 (m, 10H, 2×—OCH$_2$Ph), 7.17 (dd, 1H, 8.32 hz & 1.8 hz, Ar—H), 7.0 (d, 1H, 1.8 hz, Ar—H), 6.78 (d, 1H, 8.32 hz, Ar—H), 5.31 (br, 1H), 4.68 (s, 4H, 2×—OCH$_2$Ph), 4.1 (s, 2H), 2.65 (m, 4H), 1.85 (m, 4H), 1.28 (m,1H), 1.06 (m, 3H, CHCH$_3$).

IR(KBr)(acetate salt):—3330–3400 br, 2950, 1717, 1635, 1530, 1450, 1250, 1065, 1065 cm$^{-1}$ ESI MS(ES+): for $C_{69}H_{102}N_8O_{16}$ Calculated: 1299.602

Found:(M+Na)$^+$=1321.7 (base peak), 559.47.

UV(MeOH): $\lambda_{max}$: 208, 230, 284 nm ($\epsilon$=49233, 17260, 3249)

Compound 39:

N1-[(6S,9S,14aS,15S,16S,20S,23S,25aS,2R,11R)-12-benzyloxy-23-((1S)-2-benzyloxy-1-hydroxy-2-(4-hydroxy-3,5-di(4-methyl-1-azinanylmethyl)phenyl)ethyl)-2,11,15-trihydroxy-6-((1R)-1-hydroxyethyl)-20-hydroxymethyl-16-methyl-5,8,14,19,22,25-hexaoxoperhydrodia-zolo[2,1-c:2,1-/][1,4,7,10,13,16]hexaazacyclohenicosin-9-yl]-12-methyltetradecanamide.

Partial $^1$H NMR: 7.25–7.41 (m, 10H, 2×—OCH$_2$Ph), 7.09, 7.21 (2×s, 2H, Ar—H), 5.33 (br, 1H), 4.68 (s, 4H, 2×OCH$_2$Ph), 4.11 (s, 4H), 2.7 (m, 8H), 1.85 (m, 8H), 1.25 (m, 2H), 1.06 (m, 6H).

IR(KBr)(915/78.D,acetate salt): 3350–3450 br, 2960, 1715(sharp), 1635, 1530, 1455, 1060 cm$^{-1}$ ESI MS(ES+): for $C_{76}H_{115}N_9O_{16}$ Calculated: 1430.659

Found:(M+Na)$^+$=1432.9 1411.6, 1333.6, 1203.7, 1095.7, 808.3, 559.4, 667.6.

UV(MeOH): $\lambda_{max}$: 206, 237, 288 nm ($\epsilon$=1463, 153, 29)

Compound 40:

N1-[(6S,9S,14aS,15S,16S,20S,23S,25aS,2R,11R)-12-benzyloxy-23-((1S)-2-benzyloxy-1-hydroxy-2-(4-hydroxy-3-(4-(3-trifluromethylphenyl)-1,4-diazinan-1-ylmethyl)phenyl)ethyl)-2,11,15-trihydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16]hexaazacyclohenicosin-9-yl]-12-methyl-tetradecanamide.

Partial $^1$H NMR: 7.28–7.5 (m, 10H, 2×—OCH$_2$Ph), 7.15–7.27 (m, 4H, Ar—H), 7.12 (dd, 1H, 8.22 hz, & 1.38 hz), 7.05 (d, 1H, 1.38 hz, Ar—H), 6.85 (d, 1H, 8.22 hz, Ar—H), 5.32 (br, 1H), 4.68 (s, 4H, 2×—OCH$_2$Ph), 3.85 (s, 2H), 2.81 (m, 8H).

IR(KBr): 3300–3400 br, 2910, 2330(sharp), 1640 br, 1610, 1515, 1430, 1300, 1220, 1065 cm$^{-1}$ ESI MS(ES+): for $C_{74}H_{102}F_3N_9O_{16}$ Calculated: 1430.659

Found:(M+Na)$^+$=1452.7 1222.2 (base peak), 567.3.

Compound 41:

N1-[(6S,9S,14aS,15S,16S,20S,23S,25aS,2R,11R)-12-benzyloxy-23-((1S)-2-benzyloxy-1-hydroxy-2-(4-hydroxy-3,5-di(4-(3-trifluromethylphenyl)-1,4-diazinan-1-ylmethyl) phenyl)-ethyl)-2,11,15-trihydroxy-6-((1R)-1-hydroxyethyl)-20-hydroxymethyl-16-methyl-5,8,14,19,22,25-hexaoxoperhydrodiazolo[2,1-c:2,1-/][1,4,7,10,13,16] hexaazacyclohenicosin-9-yl]-12-methyltetradecanamide.

Partial $^1$H NMR: 7.25–7.45 (m, 10H, 2×—OCH$_2$Ph), 7.02–7.2 (m, 10H, Ar—H), 5.33 (br, 1H), 4.68 (s, 4H, 2×—OCH$_2$Ph), 3.8 (s, 4H), 2.75–2.9 (m, 16H).

IR(KBr): 3300–3400 br, 2925, 1660 br, 1610, 1540, 1455, 1330, 1260, 1075 cm$^{-1}$

ESI MS(ES+): for $C_{86}H_{115}F_6N_{11}O_{16}$

Calculated: 1672.903

Found:(M+Na)$^+$=1695.5 1222.6, 567.1.

UV(MeOH): $\lambda_{max}$: 212, 255, 282, 305 nm ($\epsilon$=41827, 20244, 4567, 2018)

Compound 42:

N1-[(6S,9S,14aS,15S,16S,20S,23S,25aS,2R,11R)-12-benzyloxy-23-((1S)-2-benzyloxy-2-(3-dibenzylaminomethyl-4-hydroxyphenyl)-1-hydroxyethyl)-2,11,15-trihydroxy-6-((1R)-1-hydro-xyethyl)-20-hydroxymethyl-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.22–7.44 (m, 20H, 2×—OCH$_2$Ph & —N(CH$_2$Ph)$_2$), 7.11 (dd, 1H, 8.6 hz & 2.2 hz, Ar—H), 7.08 (d, 1H, 2.2 hz, Ar—H), 6.81 (d, 1H, 8.6 hz, Ar—H), 5.3 (br, 1H), 4.68 (s, 4H, 2×—OCH$_2$Ph), 3.6–3.7 (s, 4H), 3.79 (s, 2H).

IR(KBr): 3300–3400 br, 2930, 1650 br, 1615(sharp), 1516, 1435, 1240, 1060 cm$^{-1}$ ESIMS(ES+): for $C_{77}H_{104}N_8O_{16}$ Calculated: 1397.706

Found: (M+Na)$^+$=1421.6 1222.8 (base peak), 1114.1, 768.8, 567.2.

UV(MeOH): $\lambda_{max}$: 210, 228, 280 nm ($\epsilon$=61484, 15835, 2697)

Compound 43:

N1-[(6S,9S,14aS,15S,16S,20S,23S,25aS,2R,11R)-23-((1S,2S)-1,2-dihydroxy-2-(3-(4-(4-fluorophenyl)-1,4-diazinan-1-ylmethyl)-4-hydroxyphenyl)ethyl)-2,11,15-trihydroxy-6-((1R)-1-hydroxyethyl)-20-hydroxymethyl-12-methoxy-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.18 (dd, 1H, 8.40 hz & 1.53 hz), 7.08 (d, 1H, 1.53 hz, Ar—H), 7.02 (d, 4H, 8.25 hz, Ar—H), 6.8 (d, 1H, 8.40 hz, Ar—H), 5.12 (d, 1H, 1.5 hz), 3.83 (s, 2H), 3.38 (s, 3H, OCH$_3$), 3.2 (br, 4H), 2.79 (br, 4H).

IR(KBr): 3300–3400br, 2930, 1645, 1620, 1510, 1440, 1380, 1230, 1070 cm$^{-1}$

ESI MS(ES+): for $C_{60}H_{92}FN_9O_{16}$

Calculated: 1214.429

Found: M+Na)$^+$=1236.7 1124.5, 1056.4 (base peak), 1012.4, 808.4, 567.2.

UV(MeOH): $\lambda_{max}$: 205, 230, 282 nm ($\epsilon$=35278, 16251, 1477)

Compound 44:

N1-[(6S,9S,14aS,15S,16S,20S,23S,25aS,2R,11R)-23-((1S,2S)-2-(3,5-di(4-(4-fluorophenyl)-1,4-diazinan-1-ylmethyl)-4-hydroxyphenyl)-1,2-dihydroxyethyl)-2,11,15-trihydroxy-6-((1R)-1-hydroxyethyl)-20-hydroxymethyl-12-methoxy-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide Partial $^1$H NMR: 7.13 (s, 2H, Ar—H), 7.0–7.1(m, 8H, Ar—H), 5.12 (br, 1H), 3.82 (s, 4H), 3.38 (s, 3H, OCH$_3$), 3.21 (br, 8H), 2.78 (br, 8H).

IR(KBr): 3300–3400br, 2930, 1645, 1620, 1510, 1440, 1380, 1230, 1070 cm$^{-1}$

ESI MS(ES+): for C$_{71}$H$_{105}$F$_2$N$_{11}$O$_{16}$
Calculated: 1406.665
Found:(M+Na)$^+$=1428.9 1249.6, 1068.4 (base peak), 839.8, 567.1.

UV(MeOH): $\lambda_{max}$: 207, 215, 234, 284 nm ($\epsilon$=46370, 30669, 14068, 2900)

Compound 45:
N1-[(6S,9S,14aS,15S,16S,20S,23S,25aS,2R,11R)-23-((1S,2S)-1,2-dihydroxy-2-(4-hydroxy-3-(4-phenyl-1,4-diazinan-1-ylmethyl)phenyl)ethyl)-2,11,15-trihydroxy-6-((1R)-1-hydroxyethyl)-20-hydroxymethyl-12-methoxy-16-methyl-5,8,14,19,22,25-hexaoxoperhydrodiazolo[2,1-c:2,1-/] [1,4,7,10,13,16]hexaazacyclohenicosin-9-yl]-12-methyltetradecanamide.

Partial $^1$H NMR: 7.22–7.35 (m, 2H, Ar—H), 7.2 (dd, 1H, 8.22 hz & 1.98 hz, Ar—H), 7.1 (d, 1H, 1.98 hz, Ar—H), 7.02 (m, 2H, Ar—H), 6.9 (m, 1H, Ar—H), 6.81 (d, 1H, 8.22 hz, Ar—H), 5.13 (d, 1H, 1.5 hz), 3.9 (s, 2H), 3.42 (s, 3H, OCH$_3$), 3.2–3.3 (br, 4H), 2.85–2.95 (br, 4H).

IR(KBr): 3350–3450 br, 2920, 1650 br, 1620, 1530, 1435, 1375, 1220, 1070 cm$^{-1}$

ESI MS(ES+): for C$_{60}$H$_{93}$N$_9$O$_{16}$
Calculated: 1196.439
Found:(M+Na)$^+$=1218.2 1056.4(base peak), 1025.1, 893.0, 567.3.

UV(MeOH): $\lambda_{max}$ 207, 232, 248, 279 nm ($\epsilon$=44536, 15767, 15368, 3562)

Compound 46:
N1-[(6S,9S,14aS,15S,16S,20S,23S,25aS,2R,11R)-23-((1S,2S)-1,2-dihydroxy-2-(3,5-di(4-phenyl-1,4-diazinan-1-ylmethyl)-4-hydroxyphenyl)ethyl)-2,11,15-trihydroxy-6-((1R)-1-hydroxy ethyl)-20-hydroxymethyl-12-methoxy-16-methyl-5,8,14,19,22,25-hexaoxoperhydrodiazolo[2,1-c:2,1-/][1,4,7,10,13,16]hexaazacyclohenicosin-9-yl]-12-methyltetradecanamide Partial $^1$H NMR: 7.24–7.41 (m, 4H, Ar—H), 7.15 (s, 2H, Ar—H), 7.0 (m, 4H, Ar—H), 6.89 (m, 2H, Ar—H), 5.1 (br, 1H), 3.83 (s, 4H), 3.4 (s, 3H, CH$_3$), 3.12–3.21 (br, 8H), 2.68–2.95 (br, 8H).

IR(KBr): 3350–3450 br, 2920, 1650 br, 1620, 1530, 1435, 1375, 1220, 1070 cm$^{-1}$

ESI MS(ES+): for C$_{71}$H$_{107}$N$_{11}$O$_{16}$
Calculated: 1370.684
Found:(M+Na)$^+$=1393.0 1232.5, 1054.3 (base peak), 1042.0.

UV(MeOH): $\lambda_{max}$: 205, 248, 279 nm ($\epsilon$=29408, 8099, 1557)

Compound 47:
N1-[(6S,9S,14aS,15S,16S,20S,23S,25aS,2R,11R)-12-benzyloxy-23-((1S)-2-(1H -1,3-diazol-1-yl)-2-(3-(1H-1,3-diazol-1-ylmethyl)-4-hydroxyphenyl)-1-hydroxyethyl)-2,11,15-trihydroxy-6-((1R)-1-hydroxyethyl)-20-hydroxymethyl-16-ethyl-5,8,14,19,22,25-hexaoxoperhydrodiazolo-[2,1-c:2,1-/][1,4,7,10,13,16] hexaazacyclohenicosin-9-yl]-12-methyltetradecanamide To a stirred solution of ornithine-5-benzylmulundocandin 2 (0.2 g, 0.182 mmol) in anhydrous N,N-dimethylformamide (10 ml) was added imidazole (0.122 g, 1.8 mmol), paraformaldehyde (0.108 g, 3.6 mmol) and heated under reflux for 15 hr. Reaction progress was monitored by TLC (20% MeOH/CHCl$_3$). The reaction work-up and purification procedure was similar to that of compound 6. Yield of the white solid 47 (0.03 g, 13.42%).

Partial $^1$H NMR: 7.8–7.7 (m, 2H, Ar—H), 7.42–7.28 (m, 5H, OCH$_2$Ph), 6.99–7.1, 7.19 (2×br, 6Hv), 6.82 (d, 1H, 8.13 hz, Ar—H), 5.32 (s, 1H), 4.67 (s, 2H, OCH$_2$Ph), 3.8 (s, 2H).

ESI MS(ES+): for C$_{62}$H$_{89}$N$_{11}$O$_{16}$
Calculated: 1228.444
Found: (M+Na)$^+$=1250.41130.4, 1063.6, 950.8, 805.7, 357.9, 259.1, 229.2(base peak).

UV(MeOH): $\lambda_{max}$ 210, 271 nm ($\epsilon$=53232, 2538)

TABLE III

| Comp. No. | Starting Compound | Secondary Amine | Paraformaldehyde | Dioxan (ml)/ React. time (hr.) | Comp. No. Yield (g, %) | M.P.(° C.) | Mole.Formula/ Mole.Weight. |
|---|---|---|---|---|---|---|---|
| 7&8 | Orn-5-benzyl MLD(2) 0.1 g, 0.091 mmol | Pyrrolidin 0.0647 g, 0.91 mmol | 0.0546 g, 1.82 mmol | 10/4 | 7 0.025 g, 23.24 | 7 145 (dec) | 7 C$_{60}$H$_{92}$N$_8$O$_{16}$ 1181.424 |
|  |  |  |  |  | 8 0.023 g, 19.98 | 8 NA | 8 C$_{65}$H$_{101}$N$_9$O$_{16}$ 1264.557 |
| 9&10 | 2 0.2 g, 0.182 mmol | 1-(2-Flurophenyl), piperazine 0.328 g, 1.82 mmol | 0.109 g, 3.64 mmol | 10/6 | 9 0.083 g, 35.31 | 9 169 | 9 C$_{66}$H$_{96}$FN$_9$O$_{16}$ 1290.527 |
|  |  |  |  |  | 10 0.105 g, 38.88 | 10 145 | 10 C$_{77}$H$_{109}$F$_2$N$_{11}$O$_{16}$ 1482.763 |
| 11&12 | 2 0.3 g, 0.273 mmol | 1-(2-Chlorophenyl), piperazine 0.536 g, 2.73 mmol | 0.163 g, 5.46 mmol | 15/5 | 11 0.16 g, 44.81 | 11 105 | 11 C$_{66}$H$_{96}$Cl N$_9$O$_{16}$ 1306.982 |
|  |  |  |  |  | 12 0.074 g, 17.87 | 12 109–110 | 12 C$_{77}$H$_{109}$Cl$_2$N$_{11}$O$_{16}$ 1515.672 |
| 13 | 2 0.2 g, 0.182 mmol | N-(α,α,α-Trifluro-m-tolyl) piperazine 0.419 g, 1.8 mmol | 0.109 g, 3.64 mmol | 10/5 | 13 0.165 g, 67.59 | 13 111 | 13 C$_{67}$H$_{96}$F$_3$N$_9$O$_{16}$ 1340.535 |

TABLE III-continued

| Comp. No. | Starting Compound | Secondary Amine | Para-formaldehyde | Dioxan (ml)/ React. time (hr.) | Comp. No. Yield (g, %) | M.P.(° C.) | Mole.Formula/ Mole.Weight. |
|---|---|---|---|---|---|---|---|
| 14&15 | 2 0.25 g, 0.228 mmol | 1-(2-Pyrimidyl), piperazine 0.347 g, 2.28 mmol | 0.136 g, 4.56 mmol | 10/5 | 14 0.078 g, 26.89 | NA | 14 $C_{64}H_{95}N_{11}O_{16}$ 1274.512 |
|  |  |  |  |  | 15 0.050 g, 15.24 | NA | 15 $C_{73}H_{107}N_{15}O_{16}$ 1450.773 |
| 16&17 | 2 0.3 g, 0.273 mmol | 1-(4-Flurophenyl), piperazine 0.492 g, 2.73 mmol | 0.163 g, 5.46 mmol | 15/5 | 16 0.22 g, 62.41 | 161 (dec) | 16 $C_{66}H_{96}FN_9O_{16}$ 1290.527 |
|  |  |  |  |  | 17 0.086 g, 21.23 | 103 | 17 $C_{77}H_{109}F_2N_{11}O_{16}$ 1482.763 |
| 18&19 | 2 0.25 g, 0.228 mmol | 1-Phenyl piperazine 0.369 g, 2.28 mmol | 0.136 g, 4.56 mmol | 10/16 | 18 0.11 g, 37.98 | 18 164 | 18 $C_{66}H_{97}N_9O_{16}$ 1272.537 |
|  |  |  |  |  | 19 0.1 g, 30.39 | 19 134 | 19 $C_{77}H_{111}N_{11}O_{16}$ 1446.782 |
| 20 | 2 0.25 g, 0.228 mmol | Dibenzylamine 0.449 g, 2.28 mmol | 0.136 g, 4.56 mmol | 10/24 | 20 0.17 g, 57.12 | 20 160–161 | 20 $C_{70}H_{98}N_8O_{16}$ 1307.582 |
| 21 | 2 0.25 g, 0.228 mmol | 1-Benzyl piperazine 0.401 g, 2.28 mmol | 0.136 g, 4.56 mmol | 10/18 | 21 0.18 g, 61.47 | 21 154 | 21 $C_{67}H_{99}N_9O_{16}$ 1286.563 |
| 22 | 2 0.194 g, 0.177 mmol | 1-(2-Pyridyl) piperazine 0.288 g, 1.77 mmol | 0.106 g, 3.54 mmol | 10/6 | 22 0.14 g, 62.24 | 22 159–161 | 22 $C_{65}H_{96}N_{10}O_{16}$ 1273.524 |
| 23&24 | 2 0.4 g, 0.364 mmol | 1-(4-Methylphenyl) piperazine 0.288 g, 1.77 mmol | 0.218 g, 7.28 mmol | 15/20 | 23 0.19 g, 40.55 | 23 140 | 23 $C_{67}H_{99}N_9O_{16}$ 1286.583 |
|  |  |  |  |  | 24 0.034 g, 6.33 | 24 166 | 24 $C_{79}H_{115}N_{11}O_{16}$ 1474.835 |
| 25 | 2 0.3 g, 0.273 mmol | 1-(4-Pyridyl) piperazine 0.445 g, 2.73 mmol | 0.163 g, 5.46 mmol | 15/7 | 25 0.207 g, 52.31 | 25 89 | 25 $C_{75}H_{109}N_{13}O_{16}$ 1448.457 |
| 26 | 2 0.35 g, 0.319 mmol | 4-Piperidino-piperidine 0.536 g, 3.19 mmol | 0.191 g, 6.38 mmol | 15/2.5 | 26 0.27 g, 66.33 | 26 87 | 26 $C_{66}H_{103}N_9O_{16}$ 1278.584 |
| 27&28 | 2 0.325 g, 0.296 mmol | 1-(2,6-Dimethyl phenyl) piperazine 0.563 g, 2.96 mmol | 0.177 g, 5.92 mmol | 15/6 | 27 0.17 g, 44.17 | 27 165 | 27 $C_{68}H_{101}N_9O_{16}$ 1300.590 |
|  |  |  |  |  | 28 g, 17.53 | 28 136 | 28 $C_{81}H_{119}N_{11}O_{16}$ 1502.889 |
| 29&30 | 2 0.35 g, 0.319 mmol | 1-(1-Phenylethyl) piperazine 0.607 g, 3.19 mmol | 0.191 g, 6.38 mmol | 15/8 | 29 0.13 g, 31.37 | 29 142 | 29 $C_{68}H_{101}N_9O_{16}$ 1300.590 |
|  |  |  |  |  | 30 0.205 g, 42.80 | 30 110 | 30 $C_{81}H_{119}N_{11}O_{16}$ 1502.889 |
| 31 | 2 0.35 g, 0.319 mmol | N-(ter.butyl) benzylamine 0.52 g, 3.19 mmol | 0.191 g, 6.38 mmol | 15/24 | 31 0.03 g, 7.39 | NA | 31 $C_{67}H_{100}N_8O_{16}$ 1273.565 |
| 32&33 | 2 0.35 g, 0.319 mmol | N-(Isopropyl) benzylamine 0.476 g, 3.19 mmol | 0.191 g, 6.38 mmol | 15/6 | 32 0.13 g, 32.39 | 32 145 | 32 $C_{66}H_{98}N_8O_{16}$ 1259.538 |
|  |  |  |  |  | 33 0.125 g, 27.61 | 33 103–105 | 33 $C_{77}H_{113}N_9O_{16}$ 1420.784 |
| 34&35 | Orn-5 & homo-Tyr-4-dibenzyl, MLD(3) 0.35 g, 0.294 mmol | Piperidine 0.250 g, 2.94 mmol | 0.176 g, 5.88 mmol | 30/31 | 34 0.17 g, 19.64 | NA | 34 $C_{68}H_{100}N_8O_{16}$ 1285.576 |
|  |  |  |  |  | 35 0.25 g, 26.88 | 35 76–80 | 35 $C_{74}H_{111}N_9O_{16}$ 1382.735 |

TABLE III-continued

| Comp. No. | Starting Compound | Secondary Amine | Para-formal-dehyde | Dioxan (ml)/ React. time (hr.) | Comp. No. Yield (g, %) | M.P.(° C.) | Mole.Formula/ Mole.Weight. |
|---|---|---|---|---|---|---|---|
| 36&37 | 3<br>0.1 g,<br>0.084 mmol | Pyrrolidin<br>0.059 g,<br>0.84 mmol | 0.0504 g,<br>1.68 mmol | 10/3 | 36<br>0.021 g,<br>19.64<br>37<br>0.05 g,<br>43.89 | 36<br>NA<br>37<br>81–83 | 36<br>$C_{67}H_{98}N_8O_{16}$<br>1271.549<br>37<br>$C_{72}H_{107}N_9O_{16}$<br>1354.682 |
| 38&39 | 3<br>0.322 g,<br>0.271 mmol | 4-Methyl piperidine<br>0.268 g,<br>2.71 mmol | 0.162 g,<br>5.42 mmol | 15/16 | 38<br>0.09 g,<br>25.56<br>39<br>0.087 g,<br>22.76 | 38<br>135–137<br>39<br>87–90 | 38<br>$C_{69}H_{102}N_8O_{16}$<br>1299.602<br>39<br>$C_{76}H_{115}N_9O_{16}$<br>1410.789 |
| 40&41 | 3<br>0.422 g,<br>0.355 mmol | N-(α,α,α-Trifluro-m-tolyl) piperazine<br>0.817 g,<br>3.55 mmol | 0.213 g,<br>7.1 mmol | 20/6 | 40<br>0.04 g,<br>7.87<br>41<br>0.35 g,<br>58.92 | 40<br>155–160<br>41<br>172–173 | 40<br>$C_{74}H_{102}F_3N_9O_{16}$<br>1430.659<br>41<br>$C_{86}H_{115}F_6N_{11}O_{16}$<br>1672.903 |
| 42 | 3<br>0.25 g,<br>0.21 mmol | Dibenzylamine<br>0.414 g<br>2.1 mmol | 0.213 g,<br>7.1 mmol | 15/18 | 42<br>0.130 g,<br>44.12 | 42<br>149–151 | 42<br>$C_{77}H_{104}N_8O_{16}$<br>1397.706 |
| 43&44 | Orn-5-methoxy, MLD(4)<br>0.3 g,<br>0.293 mmol | 1-(4-Flurophenyl) piperazine<br>0.528 g,<br>2.93 mmol | 0.175 g,<br>5.86 mmol | 15/5 | 43<br>0.19 g,<br>53.31<br>44<br>0.071 g,<br>16.99 | 43<br>191–192<br>44<br>110 | 43<br>$C_{60}H_{92}FN_9O_{16}$<br>1214.429<br>44<br>$C_{71}H_{105}F_2N_{11}O_{16}$<br>1406.665 |
| 45&46 | 4<br>0.4 g,<br>0.391 mmol | 1-Phenyl piperazine<br>0.634 g,<br>3.91 mmol | 0.234 g,<br>7.82 mmol | 20/6 | 45<br>0.23 g,<br>49.13<br>46<br>0.05 g,<br>9.3 | 45<br>114<br>46<br>NA | 45<br>$C_{60}H_{93}N_9O_{16}$<br>1196.439<br>46<br>$C_{71}H_{107}N_{11}O_{16}$<br>1370.684 |

NA = Not Available
MLD = mulundocandin

Procedure for the Preparation of Compounds 49 & 50:

To a stirred solution of mulundocandin 1 (4.8 g, 5.15 mmol) in anhydrous 1,4-dioxane (150 ml), under nitrogen atmosphere was added anhydrous methylthioglycolate (11.87 g, 111.83 mmol) and a catalytic amount of p-toluenesulfonic acid (0.338 g, 1.758 mmol) and the reaction mixture was stirred at ambient temperature for 1.5 hr. Reaction progress was monitored by TLC (20% MeOH/CHCl$_3$). TLC analysis after 1.5 hr. showed no starting compound. The reaction was quenched at 5–10° C. by the addition of saturated aqueous NaHCO$_3$ and evaporated to smaller volume (25 ml). The above mixture was diluted with water (250 ml), extracted with n-BuOH (3×150 ml), washed with water (200 ml) followed by brine (200 ml). Combined organic extract was dried over anhydrous Na$_2$SO$_4$, filtered and was concentrated in vacuum to give gummy product, which was then dissolved in a minimum amount of methanol (MeOH) (15 ml), adsorbed on silica gel (1:1 w/w), and was subjected to silica gel flash column chromatography. 0–15% MeOH/CHCl$_3$ was used as 5% step gradient elution. Evaporation of the appropriate fractions gave white compound 49 (3.171 g, 60.75%) and 49 (0.885 g, 15.69%).

Compound 49:

Methyl-2-[(6S,9S,14aS,15S,16S,20S,23S,25aS,2R,11R)-23-((1S,2S)-1,2-dihydroxy-2-(4-hydroxyphenyl)ethyl)-2,11,15-trihydroxy-6-((1R)-1-hydroxyethyl)-20-hydroxymethyl-16-methyl-9-(11-methyltridecyicarboxamido)-5,8,14,19,22,25-hexaoxoperhydrodiazolo[2,1-c:1-/][1,4,7,10,13,16]hexaazacyclohenicosin-12-ylsulfanyl] acetate.

Partial $^1$H NMR: 7.2 (d, 2H, 8.54 hz), 6.8 (d, 2H, 8.54 hz), 5.39 (br, 1H), 3.75 (s, 3H, OCH$_3$), 3.45, 3.65 (2×d, 2H, 15.78 hz).

IR(KBr): 3350, 2920, 1730, 1660–1620br, 1520, 1440, 1385, 1230, 1075 cm$^{-1}$

ESI MS(ES+): for $C_{51}H_{81}N_7O_{17}S$

Calculated: 1096.291

Found:(M+Na)$^+$=1118.5 (base peak) 1074.6, 1044.7, 1012.6, 771.3, 589.2, 567.1.

UV(MeOH): $\lambda_{max}$ pH: 206, 225, 277 nm ($\epsilon$=11990, 5769, 9428)

Compound 50:

Methyl-2-[(6S,9S,14aS,15S,16S,20S,23S,25aS,2R,11R)-2,11,15-trihydroxy-6-((1R)-1-hy-droxyethyl)-23-((1S)-1-hydroxy-2-(4-hydroxyphenyl)-2-methoxycarbonylmethylsulfanyl-ethyl)-20-hydroxymethyl-16-methyl-9-(11-methyltridecylcarboxamido)-5,8,14,19,22,25-hexaoxoperhydrodiazolo[2,1-c:1-/] [1,4,7,10,13,16] hexaazacyclohenicosin-12-ylsulfanyl]-acetate.

Partial $^1$H NMR: 7.25, 7.12 (2×d, 2H, 8.55 hz) 6.8 (2×d, 2H, 8.55 hz), 5.41 (br, 1H), 3.75 (s, 3H), 3.65, 3.8 (2×s, 3H), 3.45, 3.64 (2×d, 2H), 3.21–2.85 (m, 2H).

IR(KBr): 3300–3400 br, 2930, 1740(ester), 1680–1610 br, 1520, 1435, 1380, 1260, 1070 cm$^{-1}$ ESI MS(ES+): for $C_{54}H_{85}N_7O_{18}S_2$ Calculated: 1184.414

Found:(M+Na)$^+$=1206.6 (base peak) 1100.6, 966.5, 859.3, 808.5, 567.2.

UV(MeOH): $\lambda_{max}$: 204, 227 nm ($\epsilon$=9685, 2421)

Procedure for the Preparation of Compounds 51 & 52:—

To a stirred solution of mulundocandin 1 (2.3 g, 2.28 mmol) in anhydrous 1,4-dioxane (100 ml), under nitrogen atmosphere was added anhydrous thiophenol (4.29 g, 38.95 mmol) and a catalytic amount of p-toluenesulfonic acid (0.23 g, 1.196 mmol) and the reaction mixture was stirred at ambient temperature for 3 hr. Reaction progress was monitored by TLC (20% MeOH/CHCl$_3$). The reaction workup and purification process were similar to that described for compounds 49 and 50. Yield of the white solid 51 (1.241 g, 49.44%) and 52 (0.478 g, 17.57%).

Compound 51:

N1-[(6S,9S,14aS,15S,16S,20S,23S,25aS,2R,11R)-23-((1S,2S)-1,2-dihydroxy-2-(4-hydro-xyphenyl)ethyl)-2,11,15-trihydroxy-6-((1R)-1-hydroxyethyl)-20-hydroxymethyl-16-methyl-5,8,14,19,22,25-hexaoxo-12-phenylsulfanyl-perhydrodiazolo[2,1-c:2,1-/][1,4,7,10,13,16]hexaazacyclohenicosin-9-yl]-12-methyltetradecanamide.

Partial $^1$H NMR: 7.58 (m, 2H), 7.33 (t, 3H, 2.63 hz), 7.2 (d, 2H, 8.39 hz), 6.8 (d, 2H, 8.39 hz), 5.69 (br, 1H).

IR(KBr): 3400–3300br, 2940, 1670, 1630, 1525, 1460, 1390, 1250, 1075 cm$^{-1}$

ESI MS(ES+): for $C_{54}H_{81}N_7O_{15}S$

Calculated: 1100.326

Found:(M+Na)$^+$=1122.6 (base peak) 1078.7, 1012.5, 970.6, 808.5, 771.3, 567.3.

UV(MeOH): $\lambda_{max}$: 206, 228, 265 nm ($\epsilon$=36860, 22336, 4703)

Compound 52:

N1-[(6S,9S,14aS,15S,16S,20S,23S,25aS,2R,11R)-2,11,15-trihydroxy-6-((1R)-1-hydroxy-ethyl)-23-((1S)-1-hydroxy-2-(4-hydroxyphenyl)-2-phenylsulfanylethyl)-20-hydroxymethyl-16-methyl-5,8,14,19,22,25-hexaoxo-12-phenylsulfanylperhydrodiazolo[2,1-c:2,1-/] [1,4,7,10,13,16] hexaazacyclohenicosin-9-yl]-12-methyltetradecanamide.

Partial $^1$H NMR: 7.58 (m, 2H), 7.30 (t, 3H, 3.3 hz), 7.18–7.25(m, 5H, homo-Tyr-4-SPh), 6.91 (d, 2H, 8.4 hz), 6.61(d, 2H, 8.4 Hz), 5.69 (br, 1H).

IR(KBr): 3400–3300 br, 2940, 1680–1620 br, 1520, 1450, 1380, 1240, 1075 cm$^{-1}$

ESI MS(ES+): for $C_{60}H_{85}N_7O_{14}S_2$

Calculated: 1192.484

Found:(M+Na)$^+$=1214.6 (base peak) 1136.7, 466.5.

UV(MeOH): $\lambda_{max}$ 205, 255 nm ($\epsilon$=32415, 4892)

Compound 53:

Methyl-2-[(6S,9S,14aS,15S,16S,20S,23S,25aS,2R,11R)-23-((1S,2S)-1,2-dihydroxy-2-(4-hydroxyphenyl)ethyl)-2,11,15-trihydroxy-6-((1R)-1-hydroxyethyl)-20-hydroxymethyl-16-methyl-9-(11-methyltridecylcarboxamido)-5,8,14,19,22,25-hexaoxoperhydrodiazolo[2,1-c:1-/][1,4,7,10,13,16]hexaazacyclohenicosin-12-ylsulfonyl] acetate.

To a stirred solution of thioether 48 (0.515 g, 0.47 mmol) in 70 ml of 1:1 acetonitrile/water at ambient temperature was added OXONE® (0.577 g, 0.94 mmol). After a period of 1 hr. TLC analysis (20% MeOH/CHCl$_3$) showed conversion to a more polar product to be complete. The reaction mixture was evaporated under reduced pressure to smaller volume (25 ml). White sold precipitated out was filtered off, washed with water (25 ml) dried under high vacuum to yield nearly 90% pure sulfone 52 (0.45 g, 84.90%). This was used without purification for further reactions.(OXONE=KHSO$_5$, KHSO$_4$, K$_2$SO$_4$; 2:1:1).

Partial $^1$H NMR: 7.18 (d, 2H, 8.58 hz), 6.8 (d, 2H, 8.58 hz), 5.6 (br, 1H), 3.92–4.08 (m, 2H, SO$_2$CH$_2$CO$_2$CH$_3$), 3.85 (s, 3H, —OCH$_3$).

IR(KBr): 3500–3400 br, 2920, 2890, 1680–1625 br, 1525, 1445, 1225, 1080 cm$^{-1}$

ESI MS(ES+): for $C_{51}H_{81}N_7O_{19}S$

Calculated: 1128.289

Found:(M+Na)$^+$=1150.6 (base peak) 1034.5, 1144.6, 1012.5, 968.5, 808.6, 771.4, 567.4.

UV(MeOH): $\lambda_{max}$: 208, 223, 276 nm ($\epsilon$=43326, 31366, 3587)

Compound 54:

N1-[(6S,9S,14aS,15S,16S,20S,23S,25aS,2R,11R)-12-cyano-23-((1S,2S)-1,2-dihydroxy-2-(4-hydroxyphenyl)ethyl)-2,11,15-trihydroxy-6-((1R)-1-hydroxyethyl)-20-hydroxymethyl-16-methyl-5,8,14,19,22,25-hexaoxoperhydrodiazolo[2,1-c:2,1-/]-[1,4,7,10,13,16]hexaaza-cyclohenicosin-9-yl]-12-methyltetradecanamide.

A solution of ornithine-5-sulfone 52 (0.5 g, 0.443 mmol) and sodium cyanide (0.1 g, 2.04 mmol) in anhydrous N,N-dimethylformamide (10 ml), under nitrogen atmosphere was stirred at ambient temperature for 1 hr. Reaction progress was monitored by TLC (20% MeOH/CHCl$_3$). The reaction mixture was diluted with water (150 ml), extracted with n-BuOH (3×100 ml), washed with water (150 ml) followed by brine (150 ml). Combined organic extract was dried over anhydrous Na$_2$SO$_4$, filtered and was concentrated in vacuum to give a crude product. This was then dissolved in a minimum amount of MeOH (5 ml), adsorbed on silica gel (1:1 w/w), and was subjected to silica gel flash column chromatography. 0–20% MeOH/CHCl$_3$ was used as 5% step gradient elution. Evaporation of the appropriate fractions gave ornithine-5-cyanocompound 54 (0.16 g, 35.55%). Yield is calculated from nearly 90% pure starting compound.

Partial $^1$H NMR: 7.18 (d, 2H, 8.55 hz), 6.78 (d, 2H, 8.55 hz), 5.17 (br, 1H).

$^{13}$C NMR Spectrum: 177.08, 176.94, 174.72, 174.31, 174.17, 174.08, 173.56, 173.47, 172.98, 172.81, 172.20, 171.28, 170.73, 159.21, 133.70, 130.52, 130.24, 119.69, 118.80, 117.04, 77.41, 76.60, 72.12, 71.83, 70.65, 69.93, 69.64, 69.00, 68.83, 64.27, 63.89, 63.31, 63.08, 59.38, 59.18, 58.06, 57.04, 56.38, 54.70, 54.42, 54.21, 53.69, 53.43, 52.28, 46.13, 39.89, 39.37, 38.56, 37.63, 36.94, 36.45, 36.19, 31.19, 31.57, 31.37, 31.28, 31.14, 31.05, 28.97, 27.84, 27.55, 21.06, 20.45, 12.56, 12.19, 12.04.

IR(KBr): 3330–3400 br, 2910, 2320(CN peak), 1650, 1620, 1510, 1430, 1370, 1230, 1070 cm$^{-1}$ ESI MS(ES+): for $C_{49}H_{76}N_8O_{15}$ Calculated: 1017.178

Found:(M+Na)$^+$=1039.6 (base peak) 999.6, 995.5, 887.4, 567.4.

UV(MeOH):—$\lambda_{max}$: 205, 223, 276 nm ($\epsilon$=16989, 10046, 986)

Compound 55:

N1-[(6S,9S,14aS,15S,16S,20S,23S,25aS,2R,11R)-12-aminomethyl-23-((1S,2S)-1,2-dihydroxy-2-(4-hydroxyphenyl)ethyl)-2,11,15-trihydroxy-6-((1R)-1-hydroxyethyl)-20-hydroxy-methyl-16-methyl-5,8,14,19,22,25-hexaoxoperhydrodiazolo[2,1-c:2,1-/][1,4,7,10,13,16]hexaazacyclohenicosin-9-yl]-12-methyltetradecanamide.

To a saturated solution of ammonia in anhydrous methanol (10 ml) was added 53 (0.1 g, 0.098 mmol) and a catalytic amount of Raney Nickel (0.03 g). The reaction vessel (hydrogenation bottle, 250 ml) was evacuated by aspirator and thoroughly purged with hydrogen (three times). The resulting heterogeneous mixture was stirred under hydrogen atmosphere at 45 lb/in$^2$ pressure for 4 hr. TLC analysis (20% methanol/CHCl$_3$) showed complete conversion to a more polar product. The catalyst was filtered off through celite and the filtrate was concentrated under vacuum to give a crude product, which was subjected to reverse-phase (5 g, C-18) flash column chromatography eluting with 50–90% acetonitrile/water as 10% step gradient. Lyophilization of the appropriate fractions provided 55 (0.053 g, 52.79%).

Partial $^1$H NMR: 7.18 (d, 2H, 8.50 hz), 6.8 (d, 2H, 8.50 hz), 2.1 (m, 2H), iminol proton shifted upfield.

ESI MS(ES+): for $C_{49}H_{80}N_8O_{15}$
Calculated: 1021.210
Found:(M+Na)$^+$=1043.5 (base peak) 1019.4, 985.6, 852.8, 778.7, 760.7, 516.1, 392.4.
UV(MeOH): $\lambda_{max}$: 206, 225, 277 nm ($\epsilon$=29806, 26711, 6481)

Compound 56:
N1-[(6S,9S,14aS,15S,16S,20S,23S,25aS,2R,11R)-23-((1S,2S)-1,2-dihydroxy-2-(4-hydro-xyphenyl)ethyl)-2,11,15-trihydroxy-6-((1R)-1-hydroxyethyl)-20-hydroxymethyl-16-methyl-12-(2-morpholinoethylamino)-5,8,14,19,22,25-hexaoxoperhydrodiazolo[2,1-c:2,1-/] [1,4,7,10,13,16]hexaazacyclohenicosin-9-yl]-12-methyltetradecanamide.

To a stirred solution of ornithine-5-sulfone 52 (0.1 g, 0.089 mmol) in anhydrous 1,4-dioxane (10 ml), under nitrogen atmosphere was added 4-(2-aminoethyl) morpholine (0.495 g, 3.8 mmol) and the reaction mixture was stirred at 25–60° C. for 1 hr. Reaction progress was monitored by TLC (20% MeOH/CHCl$_3$). The reaction work-up was similar to that described for compound 54. Crude product was purified by using reverse-phase (4 g, C-18) flash column chromatography eluting with 50–90% acetonitrile/water as 10% step gradient. Lyophilization of the appropriate fractions provided 56 (0.07 g, 70.5%) Yield is calculated from nearly 90% pure starting compound.

Partial $^1$H NMR: 7.2 (d, 2H, 8.55 hz), 6.8 (d, 2H, 8.55 hz), 5.04 (br, 1H), 3.7–3.8 (m, 4H), 2.35–2.2 (m, 8H).
IR(KBr): 3300–3400 br, 2930, 1680–1620 br, 1520, 1435, 1380, 1260, 1070 cm$^{-1}$
ESI MS(ES+): for $C_{54}H_{89}N_9O_{16}$
Calculated: 1120.341
Found:(M+Na)$^+$=1142.6 (base peak) 1130.6, 540.3.

Compound 57:
N1-[(6S,9S,14aS,15S,16S,20S,23S,25aS,2R,11R)-12-(1H-1,3-diazolo-1-yl)-23-((1S,2S)-1,2-dihydroxy-2-(4-hydroxphenyl)ethyl)-2,11,15-trihydroxy-6-((1R)-1-hydroxyethyl)-20-hydroxymethyl-16-methyl-5,8,14,19,22,25-hexaoxoperhydro-diazolo[2,1-c:2,1-/][1,4,7,10,13,16]hexaazacyclohenicosin-9-yl]-12-methyl-tetradecanamide.

To a stirred solution of ornithine-5-sulfone 53 (0.1 g, 0.089 mmol) in anhydrous 1,4-dioxane (10 ml), under nitrogen atmosphere was added imidazole (0.024 g, 0.356 mmol) and the reaction mixture was stirred at 25–60° C. for 1 hr. Reaction progress was monitored by TLC (20% MeOH/CHCl$_3$). After one hour the reaction mixture was diluted with water (100 ml), extracted with n-BuOH (3×50 ml), washed with water (100 ml) followed by brine (100 ml). Combined organic extract was dried over anhydrous Na$_2$SO$_4$ and was concentrated in vacuum to give a crude product. The crude product was purified by using reverse-phase (5 g, C-18) flash column chromatography eluting with 50–90% acetonitrile/water as 10% step gradient. Lyophilization of the appropriate fractions provided 57 (0.06 g, 64.03%) Yield is calculated from nearly 90% pure starting compound.

Partial $^1$H NMR: 7.8 (s, 1H), 7.65 (br s, 2H), 7.18, (d, 2H, 8.55 hz),6.8(d, 2H, 8.55 hz), 5.30 (br s, 1H).
IR(KBr): 3350–3400 br, 2931, 1650 br, 1620, 1520, 1455, 1390, 1225, 1065 cm$^{-1}$ ESI MS(ES+) for $C_{51}H_{79}N_9O_{15}$
Calculated: 1058.230
Found: (M$^+$)=1058.6 1044.6, 1012.4, 968.5, 848.5, 771.3, 567.4

Note Starting compound (ornithine-5 and homo-tyrosine-4-disulfone mulundocandin) for the preparation of compounds 57, 58 and 59, was prepared from thioether 49 using the process outlined for preparation of compound 52.

Compound 58:
N1-[(6S,9S,14aS,15S,16S,20S,23S,25aS,2R,11R)-12-cyano-23-((1S)-2-cyano-1-hydroxy-2-(4-hydroxyphenyl)ethyl)-2,11,15-trihydroxy-6-((1R)-hydroxyethyl)-20-hydroxymethyl-16-methyl-5,8,14,19,22,25-hexaoxoperhydrodiazolo[2,1-c:2,1-/][1,4,7,10,13,16]hexaaza-cyclo henicosin-9-yl]-12-methyltetradecanamide.

Using the process outlined for the preparation of 53, a solution of ornithine-5 & homo-tyrosine-4-disulfone mulundocandin (0.5 g, 0.4 mmol) and anhydrous sodium cyanide (0.2 g, 4.08 mmol) in anhydrous N,N-dimethylformamide (10 ml), under nitrogen atmosphere was stirred at ambient temperature for 1 hr to yield dicyanomulundocandin 58 (0.19 g, 46.22%).

Partial $^1$H NMR: 7.2 (d, 2H, 8.22 hz), 6.85 (d, 2H, 8.22 hz), iminol proton shifted upfield.
IR(KBr): 3330–3400 br, 2910, 2320(CN peak), 1650, 1620, 1510, 1430, 1370, 1230, 1070 cm$^{-1}$
ESI MS(ES+): for $C_{50}H_{75}N_9O_{14}$
Calculated: 1026.189
Found:(M+Na)$^+$=1048.5 (base peak) 1004.2, 887.3.

Compound 59:
N1-[(6S,9S,14aS,15S,16S,20S,23S,25aS,2R,11R)-12-azido-23-((1R)-2-azido-1-hydroxy-2-(4-hydroxyphenyl)ethyl)-2,11,15-trihydroxy-6-((1R)-1-hydroxyethyl)-20-hydroxymethyl-16-methyl-5,8,14,19,22,25-hexaoxoperhydrodiazolo[2,1-c:2,1-/] [1,4,7,10,13,16]hexaaza-cyclo henicosin-9-yl]-12-methyltetradecanamide.

Using the process outlined for the preparation of 54, a solution of ornithine-5 & homo-tyrosine-4-disulfone mulundocandin (0.2 g, 0.16 mmol), anhydrous sodium azide (0.104 g, 1.6 mmol) in anhydrous 1,4-dioxane (10 ml), was stirred at 25–50° C. for 2 hr. Crude product was purified by using semi preparative HPLC. (semiprep RP-18 column, 250×16 mm, 10 particle size, 70% acetonitrile/water as a eluant, 8 ml/min. flow rate, $\lambda$=220 & 270 nm). Lyophilization of the appropriate fractions provided 59 (0.115 g, 67.84%). Yield is calculated from nearly 90% pure starting compound.

Partial $^1$H NMR: 7.28, 7.14 (2×d, 2H, 8.88 hz), 6.83 (t, 2H, 8.88 hz), 5.39(d, 1H, 1.86 hz).
IR(KBr): 3300–3400 br, 2930, 2100(sharp), 1650, 1620, 1515, 1440, 1240, 1070 cm$^{-1}$
ESI MS(ES+): for $C_{48}H_{75}N_{13}O_{14}$
Calculated: 1058.194
Found: (M+Na)$^+$=1080.5 1037.6, 873.9, 816.6, 567.0.
UV(MeOH): $\lambda_{max}$: 206, 221, 275 nm ($\epsilon$=21163, 8266, 1985)

Compound 60
N1-[(6S,9S,14aS,15S,16S,20S,23S,25aS,2R,11R)-2,11,15-trihydroxy-6-((1R)-1-hydroxy-ethyl)-23-((1R,2R/S)-1-hydroxy-2-(4-hydroxyphenyl)-2-(2-morpholinoethylamino)ethyl)-20-hydroxymethyl-16-methyl-12-(2-morpholinoethylamino)-5,8,14,19,22,25-hexaoxoperhydrodiazolo[2,1-c:2,1-/][1,4,7,10,13,16]hexaazacyclohenicosin-9-yl]-12-methyltetradeca-namide.

Using the process outlined for the preparation of 54, a solution of ornithine-5 & homo-tyrosine-4-disulfonemulundocandin (0.2 g, 0.16 mmol), 4-(2-aminoethyl)morpholine (0.208 g, 1.6 mmol) in anhydrous 1,4-dioxane (10 ml), was stirred at 25–50° C. for 2 hr. Crude product was purified by using semi preparative HPLC. (semiprep RP-18 column, 250×16 mm, 10μ particle size, 70% acetonitrile/water as a eluant, 8 ml/min. flow rate, λ=220 & 270 nm). Lyophilization of the appropriate fractions provided 60 (0.093 g, 43.89%). Yield is calculated from nearly 90% pure starting compound.

Partial $^1$H NMR: 7.26 (t, 2H, 8.55 hz), 6.8 (d, 2H, 8.55 hz), 5.04 (br, 1H), 3.7–3.8 (m, 8H), 2.4–2.27 (m, 16H).

IR(KBr): 3300–3400 br, 2930,1680–1620 br, 1520, 1435, 1380, 1260, 1070 cm$^{-1}$

ESI MS (ES+): for $C_{60}H_{101}N_{11}O_{16}$

Calculated: 1232.516

Found: (M+Na)$^+$=1254.8 (base peak) 1133.6, 990.6, 946.4, 302.8.

The invention claimed is:

1. A compound selected from the group consisting of a cyclohexapeptide compound of the formula (I),

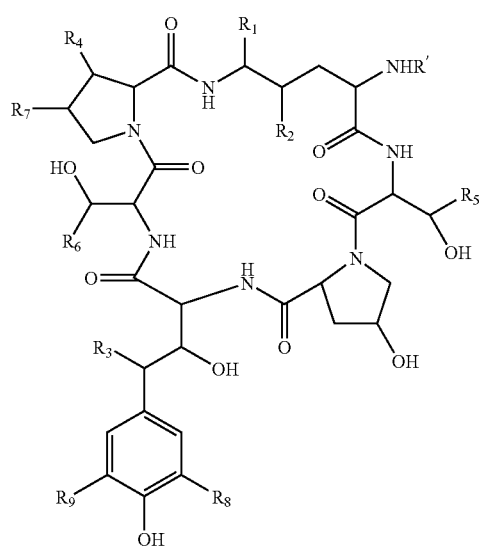

(I)

wherein,

R' is selected from the group consisting of $C_9$–$C_{20}$ alkyl; $C_9$–$C_{20}$ alkenyl; $C_9$–$C_{20}$ alkoxyphenyl, phenyl, biphenyl, terphenyl, and naphthyl; $C_1$–$C_{12}$ alkylphenyl, $C_8$–$C_{12}$ alkenylphenyl, $C_1$–$C_{12}$ alkoxyphenyl; linoleoyl; palmitoyl; 12-methylmyristoyl; 10,12-dimethylmyristoyl; and $COC_6H_4(p)OC_8H_{17}$, $R_1$ is selected from the group consisting of —CN; —CH$_2$NH$_2$; —N$_3$; aryl; substituted aryl, imidazolyl; morpholinoethylamino; —OR, wherein R is $C_1$–$C_{12}$ alkyl, substituted alkyl of (CH$_2$)$_n$—X, where n is 1–5 and X is selected from the group consisting of OH, aryl, Cl, Br, I, COOY and CN, wherein Y is selected from the group consisting of $C_1$–$C_6$ alkyl, $C_2$–$C_{12}$ alkenyl, aryl, fused aryl, substituted aryl, a heterocyclic containing 1–3 heteroatoms, mono or di-substituted aminoalkyl and a hydroxy protecting group;

$R_3$ is selected from the group consisting of —OH; —CN; —CH$_2$NH$_2$; —N$_3$; aryl; substituted aryl; heterocyclyl and substituted heterocyclyl with 1–3 of heteroatoms; aminoalkylamino; mono or di-substituted linear or cyclic aminoalkylamino; imidazolyl; —OR, wherein R $C_1$–$C_{12}$ alkyl; substituted alkyl of (CH$_2$)$_n$—X, where n is 1–5 and X is selected from the group consisting of OH, aryl, Cl, Br, I, COOY, CN, NH$_2$ and heterocyclic, wherein Y is selected from the group consisting of $C_1$–$C_6$ alkyl, $C_2$–$C_{12}$ alkenyl, aryl, fused aryl, substituted aryl, a heterocyclic containing 1–3 heteroatoms, mono or di-substituted aminoalkyl, and a hydroxy protecting group;

$R_2$ and $R_4$ are independently —H or —OH;

$R_5$ is —H or —CH$_3$;

$R_6$ is selected from the group consisting of —H, —CH$_3$ and —CH$_2$CONH$_2$;

$R_7$ is selected from the group consisting of —H, —CH$_3$ and —OH;

$R_8$ and $R_9$ are independently —H or —CH$_2$-Sec.amine in which the sec.amine is attached to —CH$_2$ through its N linkage; with the proviso that both $R_8$ and $R_9$ are not simultaneously hydrogen and wherein the secondary amine is selected from the group consisting of piperidine, pyrrolidine, 4-methylpiperidine, morpholine, dimethylamine, diisopropylamine, 4-piperidino-piperidine, piperazine, 1-methylpiperazine, 1-(2-fluorophenyl)piperazine, 1-(2-chlorophenyl)piperazine, 1-(2-pyrimidyl)piperazine, 1-(4-fluorophenyl)piperazine, N-(α,α,α-trifluoro-m-tolyl)piperazine, 1-phenylpiperazine, 1-benzylpiperazine, 1-(2-pyridyl)piperazine, 1-(4-pyridyl)piperazine, 1-(4-methylphenyl)piperazine, 1-(2,6-dimethylphenyl)piperazine, 1-(1-phenylethyl)piperazine, dibenzylamine, N-(tertbutyl)benzylamine and N-(isopropyl)-benzylamine;

and its non-toxic pharmaceutically acceptable salts.

2. The compound of claim 1 wherein $R_1$ is OR, and $R_3$ is selected from the group consisting of —OH, —OR and imidazolyl wherein R in each case is selected from the group consisting of $C_1$–$C_{12}$ alky, substituted alkyl of —(CH$_2$)$_n$—X, where n is 1–5, X is selected from the group consisting of OH, aryl, Cl, Br, I, COOY and CN, and wherein Y is selected from the group consisting of $C_1$–$C_6$ alkyl, —$C_2$–$C_{12}$-alkenyl, aryl, fused aryl, substituted aryl, a heteroaryl containing 1–3 heteroatoms, a heterocyclic containing 1–3 heteroatoms, mono or di-substituted aminoalkyl and a hydroxy protecting group.

3. The compound of claim 1 wherein R' is selected from the group consisting of linoleoyl, palmitoyl, 12-methylmyristoyl, 10,12-dimethylmyristoyl and —COC$_6$H$_4$(p)OC$_8$H$_{17}$.

4. The compound of claim 1 wherein 1) to the nitrogen atom of the secondary amine are attached at least one member of the group consisting of $C_1$–$C_{12}$ alky, $C_2$–$C_{12}$ alkenyl, aryl, substituted aryl, alkylaryl and substituted alkylaryl, or 2) the nitrogen atom of the secondary amine is part of a heterocyclic group, optionally substituted by at least one member of the group consisting of $C_1$–$C_6$ alkyl, $C_1$–$C_6$ alkenyl, aryl, amino, nitro, and halogen, or 3) the nitrogen atom of the secondary amine is part of a fused heterocyclic group, wherein the heterocyclic group contains 1–3 heteroatoms.

5. The compound of claim 1 wherein the secondary amine is selected from the group consisting of piperidine, pyrrolidine, 4-methylpiperidine, morpholine, dimethylamine, diisopropylamine, 4-piperidino-piperidine, piperazine, 1-methylpiperazine, 1-(2-fluorophenyl)piperazine, 1-(2-chlorophenyl)piperazine, 1-(2-pyrimidyl)piperazine, 1-(4-fluorophenyl)piperazine, N-(α,α,α,-trifluoro-m-tolyl)piperazine, 1-phenylpiperazine, 1-benzylpiperazine, 1-(2-pyridyl)piperazine, 1-(4-pyridyl)piperazine, 1-(4-methylphenyl)piperazine, 1-(2,6-dimethylphenyl)piperazine, 1-(1-phenylethyl)piperazine, dibenzylamine, N-(tertbutyl)benzylamine and N-(isopropyl)-benzylamine.

6. The compound of claim 1, wherein R' is 12-methylmyristoyl, $R_1$ is selected from the group consisting of —CN, —CH$_2$NH$_2$, —N$_3$, aryl, substituted aryl, —OCH$_2$C$_6$H$_4$, —OCH$_3$, —OCH$_2$OH, morpholinoethylamino and imidazolyl $R_3$ is selected from the group consisting of —OH, —CN, —CH$_2$NH$_2$, —N$_3$, aryl, substituted aryl, heterocyclyl and substituted heterocyclyl having 1–3 heteroatoms, aminoalkylamino, and mono or di-substituted linear or cyclic aminoalkylamino, $R_5$ and $R_7$ are both —CH$_3$ and $R_6$ is —H.

7. An antifungal composition comprising a fungicidally effective amount of a compound of claim 1, and a non-toxic pharmaceutically acceptable carrier.

8. A process for the production of a compound of claim 1 comprising:
   a) reacting a cyclohexapeptide compound of claim 1, wherein R', $R_2$, $R_4$, $R_5$, $R_6$ and $R_7$ are as defined in claim 1, $R_1$ and $R_3$ are both —OH, and $R_8$ and $R_9$ are —H, with an alcohol in the presence of an acid in an aprotic solvent at a temperature of 0° C. to 60° C. to obtain the corresponding cyclohexapeptide derivative of claim 1 wherein R', $R_2$, $R_4$, $R_5$, $R_6$ and $R_7$ are as defined in claim 1, $R_1$ and $R_3$ are independently —OH or —OR wherein at least one of $R_1$ or $R_3$ is —OR, R is selected from the group consisting of $C_1$–$C_{12}$ alkyl, $C_2$–$C_{12}$ alkenyl, fused aryl, substituted aryl, a heterocyclyl containing 1–3 heteroatoms, mono or di-substituted aminoalkyl; and a hydroxy protecting group, and $R_8$ and $R_9$ are —H;
   b) reacting the compound of step (a) with a secondary amine in the presence of paraformaldehyde in an aprotic solvent at a temperature of 60° C. to 150° C. to obtain the desired compound of formula I, isolating and purifying the resulting compound from the reaction mixture in a known manner and optionally converting the compound of formula I into its pharmaceutically acceptable salt in a known manner.

9. A process for the preparation of a cyclohexapeptide compound of claim 1 comprising:
   a) reacting mulundocandin of the formula (IV)

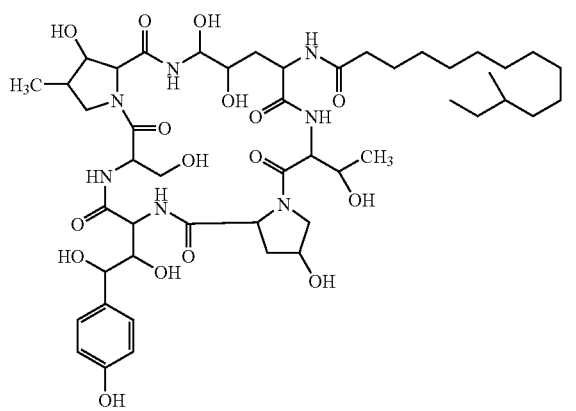

with a nucleophile in the presence of antacid in an aprotic solvent at a temperature of 0° C. to 60° C. to obtain the corresponding cyclohexapeptide derivative of the formula (V)

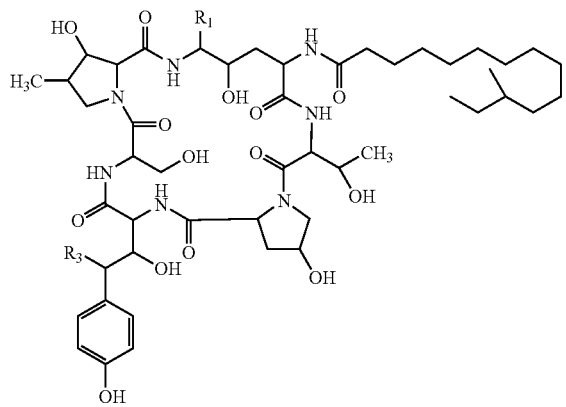

wherein $R_1$ and $R_3$ are —OH or —SR with at least one of $R_1$ or $R_3$ is —SR, R is selected from the group consisting of $C_1$–$C_{12}$ alkyl, substituted alky of —(CH$_2$)$_n$—X, where n is 1–5, X is Cl, Br, I, COOY, CN, NH$_2$ and a heterocyclic, Y is selected from the group consisting of $C_1$–$C_6$ alkyl; $C_2$–$C_{12}$ alkenyl; aryl; fused aryl; substituted aryl; a heterocyclyl containing 1–3 heteroatoms; mono or di-substituted aminoalkyl; and a hydroxy protecting group;

b) reacting the compound of step (a) with an oxidizing agent in an aqueous medium at a temperature of 20° C. to 60' to obtain the corresponding sulfones of formula V wherein $R_1$ and $R_3$ are —OH or —S(O$_2$)R, with at least one of $R_1$ or $R_3$ is —SO$_2$R, R is selected from the group consisting of $C_1$–$C_{12}$ alkyl, substituted alkyl of —(CH$_2$)$_n$—X, where n is 1–5, X is Cl, Br, I, COOY, CN, NH$_2$ and a heterocyclic, Y is selected from the group consisting of $C_1$–$C_6$ alkyl; $C_2$–$C_{12}$ alkenyl; aryl; fused aryl; substituted aryl; a heterocyclyl containing 1–3 heteroatoms; mono or di-substituted aminoalkyl; and a hydroxy protecting group;

c) reacting the sulfone of step(b) with a secondary amine in a solvent at a temperature of 20° C. to 60° C. to obtain the desired compound of claim 1, isolating and purifying the resulting compound and optionally converting the compound of claim 1 into its pharmaceutically acceptable salt in a known manner.

* * * * *